(12) United States Patent
Yada et al.

(10) Patent No.: US 7,368,601 B2
(45) Date of Patent: May 6, 2008

(54) PROCESS FOR PRODUCING (METH)ACRYLIC ACIDS AND PROCESS FOR DISTILLING THE SAME

(75) Inventors: Shuhei Yada, Yokkaichi (JP); Yasushi Ogawa, Yokkaichi (JP); Yoshiro Suzuki, Yokkaichi (JP); Kimikatsu Jinno, Yokkaichi (JP); Hirochika Hosaka, Yokkaichi (JP); Kenji Takasaki, Yokkaichi (JP); Masayasu Goriki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/526,730

(22) Filed: Sep. 26, 2006

(65) Prior Publication Data

US 2007/0021633 A1    Jan. 25, 2007

Related U.S. Application Data

(60) Division of application No. 10/817,955, filed on Apr. 6, 2004, which is a continuation of application No. PCT/JP02/10411, filed on Oct. 7, 2002.

(30) Foreign Application Priority Data

| Oct. 9, 2001 | (JP) | ............................. 2001-310894 |
| Dec. 3, 2001 | (JP) | ............................. 2001-368666 |
| Dec. 11, 2001 | (JP) | ............................. 2001-377723 |
| Dec. 20, 2001 | (JP) | ............................. 2001-387244 |
| May 15, 2002 | (JP) | ............................. 2002-72434 |

(51) Int. Cl.
*C07C 51/42* (2006.01)

(52) U.S. Cl. ..................................... 562/600

(58) Field of Classification Search ..................... None
See application file for complete search history.

(56) References Cited

U.S. PATENT DOCUMENTS

| 3,717,553 | A | 2/1973 | Otsuki et al. |
| 5,728,272 | A | 3/1998 | Hammon et al. |
| 6,409,886 | B1 | 6/2002 | Matsumoto et al. |
| 6,635,148 | B1 | 10/2003 | Nishimura et al. |
| 6,651,731 | B2 | 11/2003 | Nishimura et al. |
| 6,695,928 | B1 * | 2/2004 | Nakahara et al. ............. 134/26 |
| 2002/0008010 | A1 | 1/2002 | Hamamoto et al. |

(Continued)

FOREIGN PATENT DOCUMENTS

EP    1033359 A2    9/2000

(Continued)

*Primary Examiner*—Karl Puttlitz
(74) *Attorney, Agent, or Firm*—Nixon & Vanderhye P.C.

(57) ABSTRACT

In the stopping and starting operations of a distillation column used for producing (meth)acrylic acids according to the present invention, upon stopping the operation of the distillation column, the heating of a reboiler attached thereto is interrupted and then the reboiler is rapidly cooled; and/or upon starting the operation of the distillation column for production of the (meth)acrylic acids, an inner wall surface of the distillation column is heated to a temperature higher than a condensation temperature of the (meth)acrylic acids and the operation of the distillation column is started under the heated condition. According to the present invention, it is possible to early and safely stop the operation of the distillation column while preventing the occurrence of polymerization within the distillation column, and stably perform an operation for distillation of acrylic monomers for a long period of time.

9 Claims, 5 Drawing Sheets

U.S. PATENT DOCUMENTS

| | | |
|---|---|---|
| 2002/0027067 A1 | 3/2002 | Hamamoto et al. |
| 2002/0104644 A1 | 8/2002 | Nishimura et al. |
| 2004/0050681 A1 | 3/2004 | Nishimura et al. |
| 2004/0260122 A1 | 12/2004 | Yada et al. |

FOREIGN PATENT DOCUMENTS

| | | |
|---|---|---|
| EP | 1043050 A2 | 10/2000 |
| EP | 1044957 A1 | 10/2000 |
| EP | 1057804 A2 | 12/2000 |
| FR | 2201275 | 4/1974 |
| FR | 2801306 | 5/2001 |
| JP | 48-32513 | 10/1973 |
| JP | 49-15153 | 4/1974 |
| JP | 63-275544 | 11/1988 |
| JP | 07-265817 | 10/1995 |
| JP | 2000-355570 | 12/2000 |
| JP | 2001-213839 | 8/2001 |
| JP | 2001340701 | 12/2001 |
| JP | 2002-226427 | 8/2002 |

* cited by examiner

PROCESS FOR PRODUCING (METH)ACRYLIC ACIDS AND PROCESS FOR DISTILLING THE SAME

This application is a divisional of application Ser. No. 10/817,955 filed Apr. 6, 2004, which in turn is a continuation of PCT International Application No. PCT/JP02/10411, filed in Japanese on 07 Oct. 2002, which designated the US. PCT/JP02/10411 claims priority to JP Application No. 2001-310894 filed 09 Oct. 2001, JP Application No. 2001-368666 filed 03 Dec. 2001, JP Application No. 2001-377723 filed 11 Dec. 2001, JP Application No. 2001-387244 filed 20 Dec. 2001 and JP Application No. 2002-72434 filed 15 Mar. 2002. The entire contents of these applications are incorporated herein by reference.

TECHNICAL FIELD

The present invention relates to a process for producing (meth)acrylic acids and a process for distilling the (meth) acrylic acids. More particularly, the present invention relates to a method for preventing the polymerization of monomers which is frequently caused when acrylic acid, methacrylic acid or esters of these acids obtained by catalytic gas-phase oxidation of propane, propylene or isobutylene are subjected to separation, concentration and purification by a distillation method. Further, the present invention relates to a method for early and safely stopping an operation of a distillation column while preventing the occurrence of polymerization reaction within the distillation column. Also, the present invention relates to a methord for washing the distillation column as well as a handling device including conduits.

Meanwhile, in the present specification, the "(meth) acrylic acid" used herein means either one or both of acrylic acid and methacrylic acid, and acrylic acid, methacrylic acid or esters of these acids may be occasionally referred to as "(meth)acrylic acids" or "acrylic monomers".

BACKGROUND ART

In general, (meth)acrylic acids are separated or purified by a distillation method.

In recent years, for the purposes of improving a separation efficiency by distillation, increasing a throughput from distillation, etc., high-performance fillers have been developed and now used in distillation columns for various processes. However, since the (meth)acrylic acids are extremely readily polymerized, the conventional tray-type distillation columns, especially high-performance packed columns, still suffer from significant problems such as undesired production of polymers within these distillation columns.

Hitherto, as the method for preventing the production of polymers of the (meth)acrylic acids, there have been proposed the method of improving a tray structure of a distillation column (Japanese Patent Application Laid-Open (KOKAI) No. 2000-300903), the method using a specific polymerization inhibitor (Japanese Patent Application Laid-Open (KOKAI) No. 7-53449) and the like. However, these conventional methods still fail to allow a continuous operation of the distillation column for a long period of time, and require periodic inspection, washing and repair thereof, etc., which must be accompanied with stopping of its operation. The polymers are frequently produced from the beginning of operation of the distillation column. Once such polymers are produced, a stable flow of gases or liquids within the distillation column is disturbed, thereby frequently causing such a phenomenon that production of the polymers is further promoted.

Some of the above distillation columns are equipped with a reboiler (heat exchanger for heating) for heating a part of a bottom liquid removed from the distillation column and then returning the thus heated liquid back to a bottom of the distillation column. In addition, some of the distillation columns may be equipped with a reflux tank for condensing a distillate removed from a top of the distillation column and then returning a part of the resultant condensate to the distillation column in order to enhance a recovery percentage and purity of aimed products distilled.

Conventionally, upon stopping an operation of the above-described reduced-pressure type distillation column, the heating of the reboiler is interrupted, and an inside of the distillation column is returned to an ordinary pressure by feeding an inert gas such as nitrogen thereinto.

However, in the conventional methods of stopping the operation of the above reduced-pressure type distillation column, the inert gas such as nitrogen is fed into the distillation column before the inside of the distillation column reaches a sufficiently low temperature, namely under such a condition that the distillation column is still filled with a large amount of vapors of the (meth)acrylic acids containing no polymerization inhibitor. Therefore, the (meth)acrylic acids tends to undergo polymerization to produce polymers thereof. The removal of the polymers thus produced within the distillation column requires complicated procedures, resulting in problems such as increased maintenance costs and prolonged working time upon its periodic maintenance or repair.

Meanwhile, when the inside of the distillation column is returned to an ordinary pressure by feeding a gas having a polymerization-inhibiting effect such as air into the distillation column in order to prevent the occurrence of polymerization reaction upon stopping the operation of the distillation column, an inside atmosphere of the distillation column may fall within an explosion range. Therefore, such a method cannot be adopted for the above purpose. Further, in the case where the inert gas is fed after the inside temperature of the distillation column is sufficiently lowered, it takes a long period of time until sufficiently cooling the distillation column, i.e., until feeding the inert gas thereinto, resulting in poor operation efficiency.

Meanwhile, it will be suggested that after discharging a whole bottom liquid in the distillation column, the liquid stored in the reflux tank is refluxed thereinto to cool an inside of the distillation column and then return an inside pressure thereof to an ordinary pressure. However, only the liquid in the reflux tank is insufficient to cool the inside of the distillation column. In addition, when the high-temperature bottom liquid is transferred into a tank, undesirable polymerization of the (meth)acrylic acids may be induced due to temperature rise in the tank.

On the other hand, as the above periodic washing and repairing method, Japanese Patent Application Laid-Open (KOKAI) No. 2000-319223 has proposed the method of washing a distillation column with a base solution containing a base substance such as sodium hydroxide and potassium hydroxide, and then washing with a solvent (more preferably water). However, according to the present inventors' knowledge, this method fails to remove polymers and solids precipitated in the column to a sufficient extent.

More specifically, the solids derived from the (meth) acrylic acid and/or (meth)acrylic esters is enhanced in absorption property thereof by the alkali substance, and swelled up even with a slight amount of water. The water-swelled solids (swelled solid matters) exhibit a stickiness (under gelled condition) and, therefore, is not easy to separate and peel from portions onto which the solids are adhered or deposited. Also, at the portions of the distillation column to which the aqueous alkali solution is hardly reached, such as a rear side of respective trays, it may be difficult to remove the solids adhered or deposited thereto.

The present invention has been attained to solve the above problems. Objects of the present invention are as follows:

(1) To provide a method for preventing polymerization of monomers frequently caused upon separation and purification of (meth)acrylic acids. In particular, to provide a method of keeping an inside of a distillation column in such an atmosphere in which the (meth)acrylic acids are hardly polymerized, upon starting or re-staring the distillation procedure.

(2) To provide a method for early and safely stopping an operation of the distillation column in which the polymerizable (meth)acrylic acids are distilled under reduced pressure, by preventing the polymerization within the distillation column.

(3) To provide a method for washing the distillation column in which crude (meth)acrylic acids are separated and purified. In particular, to provide a method for efficiently washing the distillation column while preventing impurities from being mixed in the (meth)acrylic acids and recovering useful materials by using various substances obtained from processes conducted before or after the distillation column, in the process for production of the (meth)acrylic acids.

(4) To provide a method for preventing polymerization of monomers frequently caused upon separation and purification of an acrylic monomer. In particular, to provide a method of keeping an inside of a distillation column in such an atmosphere in which the acrylic monomer is hardly polymerized, upon starting or re-staring the distillation procedure.

(5) To provide a method for handling the above compounds which is improved so as to efficiently wash out and remove solids derived from (meth)acrylic acid and/or (meth)acrylic esters, adhered onto the surface of a handling device including conduits.

DISCLOSURE OF THE INVENTION

Figure 1:
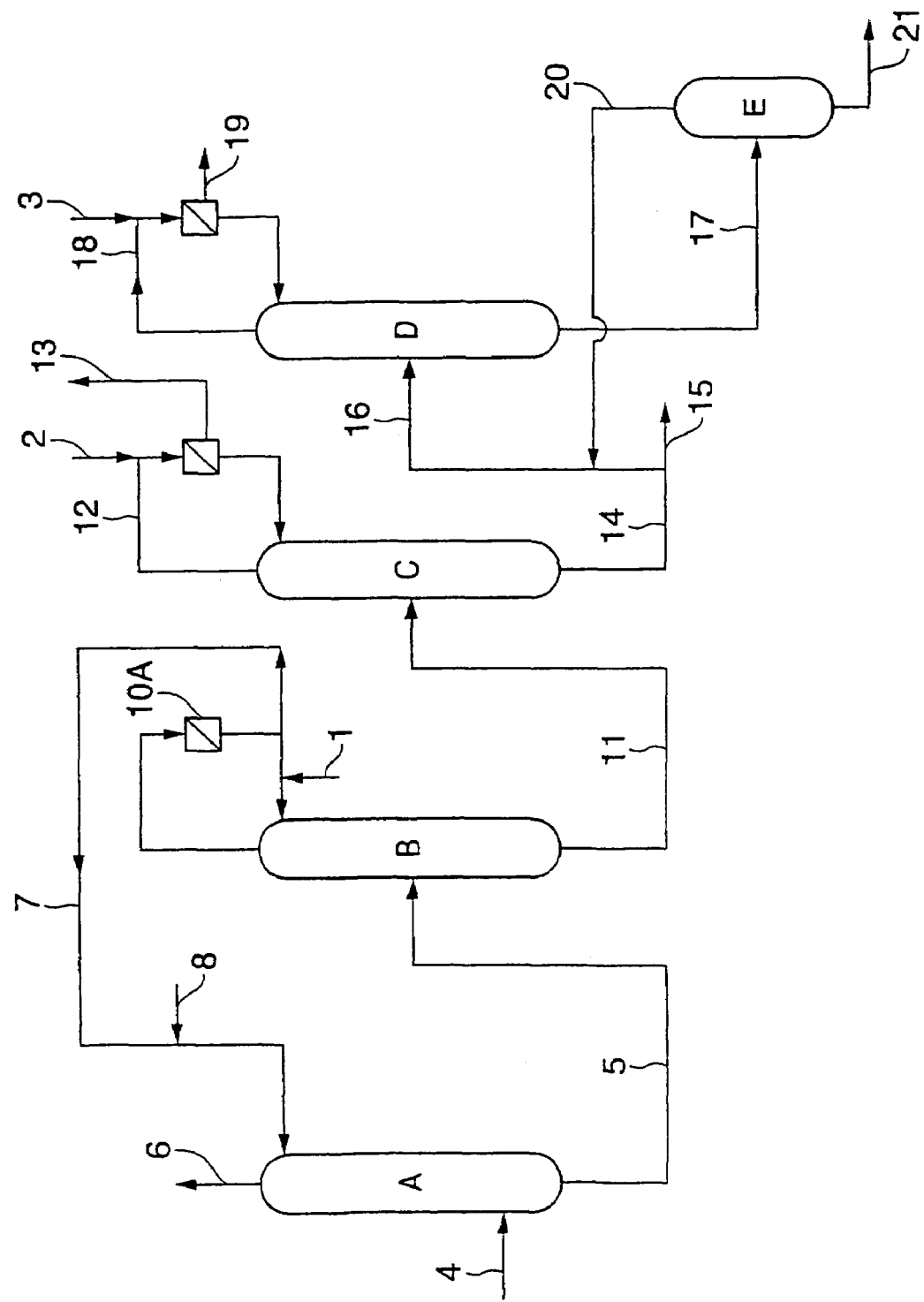
FIG. 1 is an example of a flow diagram showing a process for producing acrylic acid from raw propylene.

According to the present invention, there are provided a series of plural aspects closely related to each other. The respective aspects of the present invention are as follows.

(I) A process for producing (meth)acrylic acids including stopping and starting operations of a distillation column used therefor, comprising:

upon stopping the operation of the distillation column, interrupting heating of a reboiler attached thereto, and then rapidly cooling the reboiler; and/or upon starting the operation of the distillation column for production of the (meth)acrylic acids, heating an inner wall surface of the distillation column to a temperature higher than a condensation temperature of the (meth)acrylic acids, and starting the operation of the distillation column under the heated condition.

(II) A method for distilling acrylic acid, methacrylic acid or esters thereof using a distillation column, comprising:

previously heating an inner wall surface of the distillation column to a temperature higher than a condensation temperature of the acrylic acid, methacrylic acid or esters thereof; and starting an operation of the distillation column under the heated condition.

In particular, the above-mentioned aspects of the present invention have accomplished the above object (1), and been attained on the basis of the following present inventors' knowledge.

That is, in the case where once polymers are produced, an inside of the distillation column is partially clogged, thereby disturbing a flow of gases and liquids therein. As a result, the production of the polymers is further promoted. Therefore, it is extremely important to prevent polymerization of the (meth)acrylic acids at the beginning of the distillation procedure. The above object (1) can be accomplished by keeping the inner wall surface of the distillation column at a specific high temperature.

(III) A method for stopping an operation of a distillation column with a reboiler for purifying (meth)acrylic acids by distillation, comprising:

upon interrupting supply of the (meth)acrylic acids to the distillation column to stop the operation of the distillation column, interrupting heating of the reboiler and then rapidly cooling the reboiler.

In particular, this aspect of the present invention has accomplished the above object (2), and been attained on the basis of the following present inventors' knowledge.

That is, after heating of the reboiler is interrupted, the reboiler is rapidly cooled to sufficiently reduce the inside temperature of the distillation column. Thereafter, the inert gas is fed into the distillation column to return the inside pressure thereof to an ordinary pressure, thereby preventing the (meth)acrylic acids from being polymerized in the distillation column. Specifically, the inert gas used for returning the inside pressure of the distillation column to an ordinary pressure, is fed into the distillation column whose inside temperature has been sufficiently reduced. In the distillation column having the sufficiently reduced inside temperature, the amount of the (meth)acrylic acids that are present as a vapor containing no polymerization inhibitor, is reduced, so that the polymerization thereof can be prevented.

In addition, a forced circulation pump (reboiler pump) is preferably provided on a bottom liquid circulation line including the reboiler in order to enhance the cooling efficiency.

Meanwhile, the inside temperature of the distillation column may also be reduced by returning a reflux liquid stored in a reflux tank to the distillation column. However, the rapid cooling of the reboiler according to the present invention can provide the following advantages and excellent effects as compared to the above method of returning the reflux liquid in the reflux tank to the distillation column.

(a) Economical advantages:

The capacity of the bottom liquid circulation pump of the reboiler (reboiler pump) is usually 10 to 20 times a capacity of a pump for the reflux liquid (reflux pump). In general, the reflux pump is an expensive pump having a large delivery pressure which has a high head, i.e., is capable of a high-pressure output, but the reflux pump frequently actually used has a small flow amount. On the contrary, the reboiler pump exhibits a low-head output and has a large flow amount. For this reason, when the reflux pump is used for cooling, the cooling time is generally prolonged as compared to the cooling by the reboiler pump. In order to achieve the cooling procedure using the reflux pump for a similar period to that of the rapid cooling as aimed by the present invention, the high-head reflux pump must be modified in its design so as to have a large flow amount, resulting in increased installation costs. On the other hand, according to the present invention, the rapid cooling can be efficiently performed using the inexpensive reboiler pump.

(b) Operational advantages:

The easily-polymerizable (meth)acrylic acids tend to be polymerized at a higher temperature. On the other hand, in the distillation column, the temperature increases from a top thereof toward a bottom thereof. Therefore, in the case where the bottom of the distillation column where the temperature is highest, is cooled by rapidly cooling the reboiler, the polymerization of the (meth)acrylic acids can be effectively avoided.

In the present invention, it is preferred that the reboiler is rapidly cooled by feeding a cooling medium thereto. Upon the rapid cooling of the reboiler, the bottom temperature of the distillation column is preferably reduced to not more than 50° C. Also, upon stopping the operation of the distillation column, the inside of the distillation column is preferably cooled by feeding the liquid stored in the reflux tank into the distillation column.

However, in the present invention, since the inside of the distillation column is sufficiently cooled by the rapid cooling of the reboiler, the additional cooling using the reflux liquid in the reflux tank is not necessarily required. More specifically, the distillation column has a temperature distribution or gradient varying from the top toward the bottom. Therefore, when the heating of the reboiler is interrupted, the heat of burning from the bottom is no longer supplied, resulting in reduction in temperature of the top liquid. The low-temperature top liquid is flowed down, thereby cooling not only an upper portion of the distillation column, but also a large amount of gases of the (meth)acrylic acids present therein. For this reason, the upper portion of the distillation column can be sufficiently cooled without flowing the reflux liquid therethrough. Further, the rapid cooling of the reboiler prevents a fresh vapor of the (meth)acrylic acids from being further produced. The use of the method of flowing the reflux liquid in combination with the rapid cooling of the reboiler is, as a matter of course, more effective.

Thus, it is preferred that after the bottom temperature of the distillation column is cooled to not more than 50° C. by cooling the inside thereof, the inert gas is fed into the distillation column in order to return the inside pressure thereof to an ordinary pressure.

(IV) A process for producing purified (meth)acrylic acids by distilling (meth)acrylic acids using a distillation column including stopping and starting operations of the distillation column, comprising:

successively washing the distillation column with the following washing agents:

(1) water;

(2) an aqueous alkali solution; and (3) an organic solvent.

(V) A process for producing purified (meth)acrylic acids by distilling (meth)acrylic acids using a distillation column including stopping and starting operations of the distillation column, comprising:

successively washing the distillation column with the following washing agents:

(1) water;

(2) an aqueous alkali solution;

(2a) water; and (3) an organic solvent.

In particular, the above aspects (IV) and (V) of the present invention have accomplished the above object (3), and been attained on the basis of the following present inventors' knowledge.

(1) Clogging substances produced in the distillation column are composed mainly of acid polymers obtained by polymerization of the (meth)acrylic acids, and readily dissolved in the aqueous alkali solution.

(2) Alkali components are effectively removed by washing with water.

(3) In the case where a large amount of water is present within the distillation column, it takes a long period of time until reaching normal operation conditions after restarting the operation thereof.

(4) The production of polymers is more frequently caused during an unstable operation period after restarting the operation of the distillation column.

(5) The production of polymers can be remarkably inhibited by dehydrating an inside of the distillation column.

(6) Various organic solvent-based substances obtained from processes conducted before or after the distillation column can be efficiently-used as the dehydrating agent.

(7) In the case where residual alkali components are present, the (meth)acrylic acids tend to be decomposed.

(VI) A method for distilling acrylic acid, methacrylic acid and esters of these acids using a distillation column, comprising:

previously wetting an inner wall surface of the distillation column with a polymerization inhibitor-containing liquid; and then starting an operation of the distillation column.

In particular, the above aspect of the present invention have accomplished the above object (4), and been attained on the basis of the following present inventors' knowledge.

That is, In the case where once polymers are produced, the inside of the distillation column is partially clogged, thereby disturbing a suitable flow of gases and liquids therein. As a result, the production of the polymers is further promoted. It is extremely important to prevent polymerization of the acrylic monomer at an early stage after starting the operation of the distillation column. The above object (4) can be accomplished by appropriately modifying a using form of the polymerization inhibitor.

(VII) A method for washing out and removing a solid derived from polymerizable compounds including (meth)acrylic acid and/or (meth)acrylic esters, which is adhered onto surface of a handling device including conduits, comprising:

using a volatile base substance as a washing agent therefor.

In particular, the above aspect of the present invention have accomplished the above object (5), and been attained on the basis of the following present inventors' knowledge.

That is, properties of the solids swelled by action of the aqueous alkali solution vary depending upon the alkali used. In the case where weak alkali such as volatile base substances, typically ammonia, is used as the alkali, the obtained swelled solids show a low viscosity. Also, since the volatile base substances are diffused together with steam into every corners, it becomes possible to remove even the solids adhered to portions to which the aqueous alkali solution is hardly reached.

The present invention will be described in detail below.

<Outline of the Invention>

Mixtures to be distilled according to the present invention include acrylic acid, methacrylic acid or esters of these acids, namely (meth)acrylic acids. These compounds may be occasionally referred to as acrylic monomers. For example, the processes of the present invention can be applied to acrylic acid produced by subjecting propane to gas-phase catalytic oxidation in the presence of a catalyst such as a Mo—V—Te-based composite oxide catalyst and a Mo—V—Sb-based composite oxide catalyst, or (meth) acrylic acid produced by subjecting propylene or isobutylene to gas-phase catalytic oxidation in the presence of a Mo—Bi-based composite oxide catalyst to obtain acrolein or methacrolein, and then subjecting the thus obtained acrolein or methacrolein to gas-phase catalytic oxidation in the presence of a Mo—V-based composite oxide catalyst. The above production process of the (meth)acrylic acid may be performed by a two stage reaction method in which the former reaction for oxidizing propylene to produce mainly acrolein and the latter reaction for oxidizing the thus produced acrolein to obtain mainly acrylic acid are conducted by separate reactors, or one stage reaction method in which both catalysts for the former and latter reactions are filled into one reactor to simultaneously conduct both the reactions therein. Further, (meth)acrylic esters obtained by using (meth)acrylic acid as a raw material can also be treated according to the present invention.

Examples of the acrylic esters may include methyl acrylate, ethyl acrylate, butyl acrylate, isobutyl acrylate, tert-butyl acrylate, 2-ethylhexyl acrylate, 2-hydroxyethyl acrylate, 2-hydroxypropyl acrylate, methoxyethyl acrylate or the like, and examples of the methacrylic esters may include similar corresponding compounds thereof.

The reaction mixture obtained by the above gas-phase catalytic oxidation is absorbed into water to thereby obtain an aqueous solution containing (meth)acrylic acid. The thus obtained aqueous solution is concentrated in the presence of an azeotropic agent such as alcohols, ketones and aromatic hydrocarbons to obtain crude (meth)acrylic acid. As the azeotropic agent, there may be especially preferably used methyl ethyl ketone, methyl isobutyl ketone, benzene and toluene.

The thus produced non-purified acrylic monomer contains high-boiling impurities such as dimers, trimers or tetramers of the acrylic monomer, esterified products of these oligomers, maleic anhydride, benzaldehyde, β-hydroxypropionic acid, β-hydroxypropionic acid esters, β-alkoxypropionic acid and β-alkoxypropionic acid esters. In the present invention, the content of the acrylic monomer in the mixture fed to the distillation column is usually not less than 2% by weight, preferably not less than 5% by weight, more preferably not less than 10% by weight. Although the acrylic monomer is present at a low concentration, the mixture or composition containing, in addition to the acrylic monomer, impurities and/or water tends to be extremely readily polymerized under temperature and pressure conditions used upon conducting the distillation treatment within the distillation column. In addition, such a polymerization tends to be caused at an initial stage of the distillation treatment. Accordingly, since the present invention is applied to a broader range, even the process liquid containing a small amount of the acrylic monomer can be extremely effectively treated.

That is, the distillation of the (meth)acrylic acids (acrylic monomers) according to the present invention usually means a process (purification process) for obtaining high-purity acrylic monomers. However, the present invention is not limited to this process, and can also be applied to such a process for recovering (separating and concentrating) acrylic monomer-rich components from the mixture containing the acrylic monomers.

Next, the process shown in FIG. 1 is explained. In FIG. 1, reference character A represents an acrylic acid collection column, B is a dehydration column, C is a low-boiling fraction separation column (acetic acid separation column), D is a high-boiling fraction separation column (acrylic acid purification column), and E is a high-boiling fraction decomposition column.

An acrylic acid-containing gas obtained by subjecting propylene and/or acrolein to catalytic gas-phase oxidation using a molecular oxygen-containing gas, is introduced into the acrylic acid collection column A through a line 4, and contacted therein with water to obtain an aqueous acrylic acid solution.

Then, the thus obtained aqueous acrylic acid solution is fed to the dehydration column B. The dehydration column B is supplied with an azeotropic agent to distil out an azeotropic mixture composed of water and the azeotropic agent from a top thereof, and to obtain acrylic acid containing acetic acid from a bottom thereof. The azeotropic mixture composed of water and the azeotropic agent, which is distilled from a top thereof, is then introduced into a storage tank 10A where the mixture is separated into an organic phase composed mainly of the azeotropic agent and an aqueous phase composed mainly of water. The organic phase is circulated to the dehydration column B, whereas the aqueous phase is circulated to the acrylic acid collection column A through a line 7 where the aqueous phase is can be usefully used as a collecting water that is contacted with the acrylic acid-containing gas. If required, water is replenished to the acrylic acid collection column A through a line 8. In addition, in order to recover the azeotropic agent from the process liquid flowed through the line 7, the process liquid may be circulated to the acrylic acid collection column A through an azeotropic agent recovery column (not shown).

The crude acrylic acid removed from the bottom of the dehydration column B through a line 11 is introduced into the low-boiling fraction separation column (acetic acid separation column) C in order to remove residual acetic acid therefrom. In the low-boiling fraction separation column C, acetic acid is separated and removed from the crude acrylic acid, and discharged from a top thereof through lines 12 and 13. Since the acetic acid flowed through the line 13 contains acrylic acid, a part or whole amount thereof may be returned to the process. On the other hand, acrylic acid containing substantially no acetic acid is obtained from the bottom of the low-boiling fraction separation column C through a line 14. The thus obtained acrylic acid has a considerably high purity and, therefore, can be directly used as a raw material for production of acrylic esters. In some cases, the acrylic acid may be fed through a line 15 to obtain acrylic acid as a product. In order to obtain acrylic acid having a still higher purity, the acrylic acid is introduced into the high-boiling fraction separation column (acrylic acid purification column) D through a line 16 to separate and remove high-boiling fractions therefrom. The thus separated high-boiling fractions are discharged from the bottom of the column D through a line 17, whereas a high-purity acrylic acid is recovered from the top of the column D through lines 18 and 19. The high-boiling fractions discharged through the line 17 is then introduced into the high-boiling fraction decomposition column E, and a part of decomposed products is recovered as acrylic acid, and circulated to the process through a line 20. The high-boiling substances obtained in the high-boiling fraction decomposition column E are separated and removed through a line 21.

In the present process, the polymerization inhibitor may be fed from one or two or more of lines 1 to 3.

Figure 2:
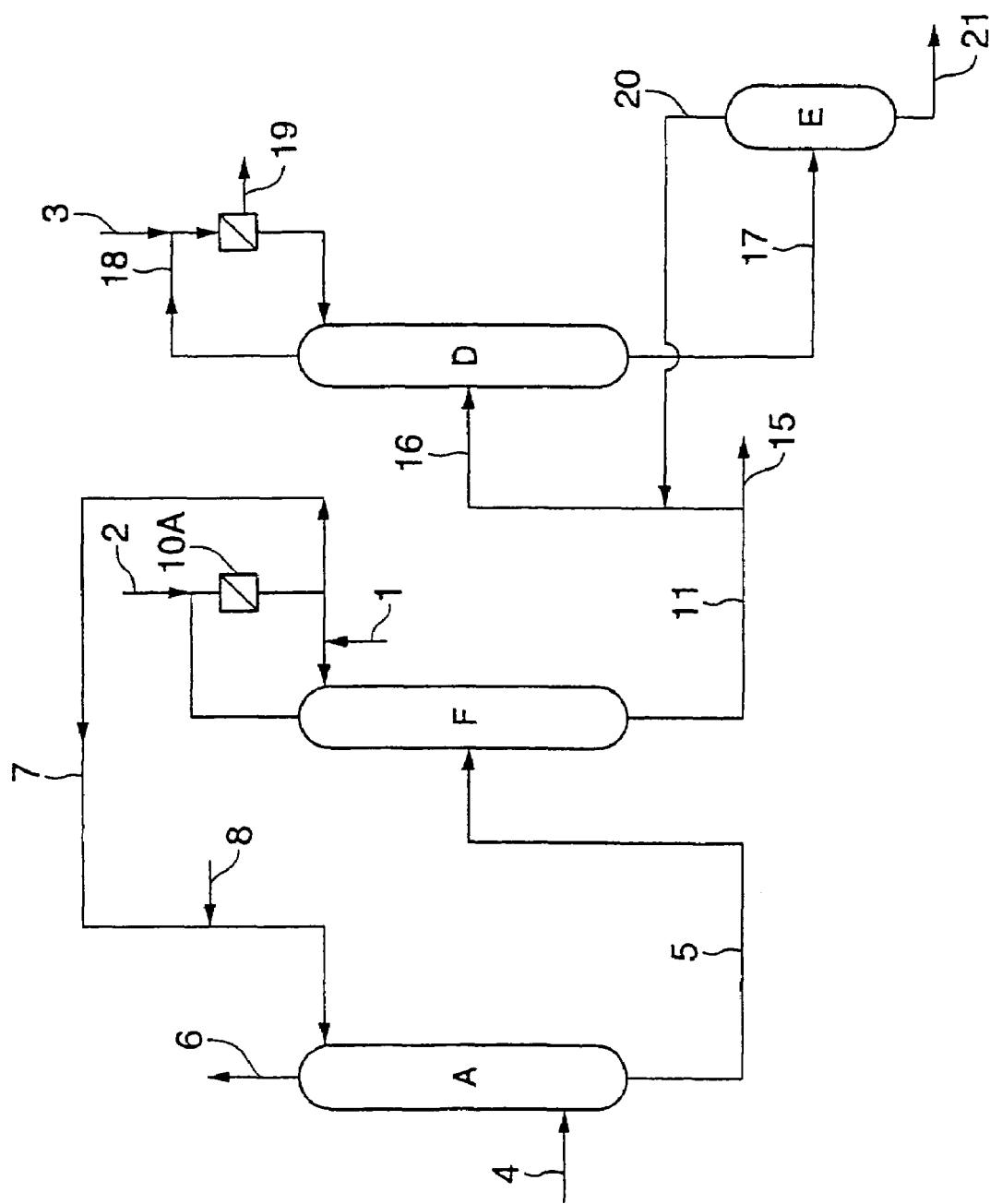
FIG. 2 is another example of a flow diagram showing a process for producing acrylic acid from raw propylene.

Next, the process shown in FIG. 2 is explained. The process shown in FIG. 2 is basically the same in flow of substances as that shown in FIG. 1 except that the dehydration column B and the low-boiling fraction separation column (acetic acid separation column) C are integrated into one distillation column F.

Figure 3:
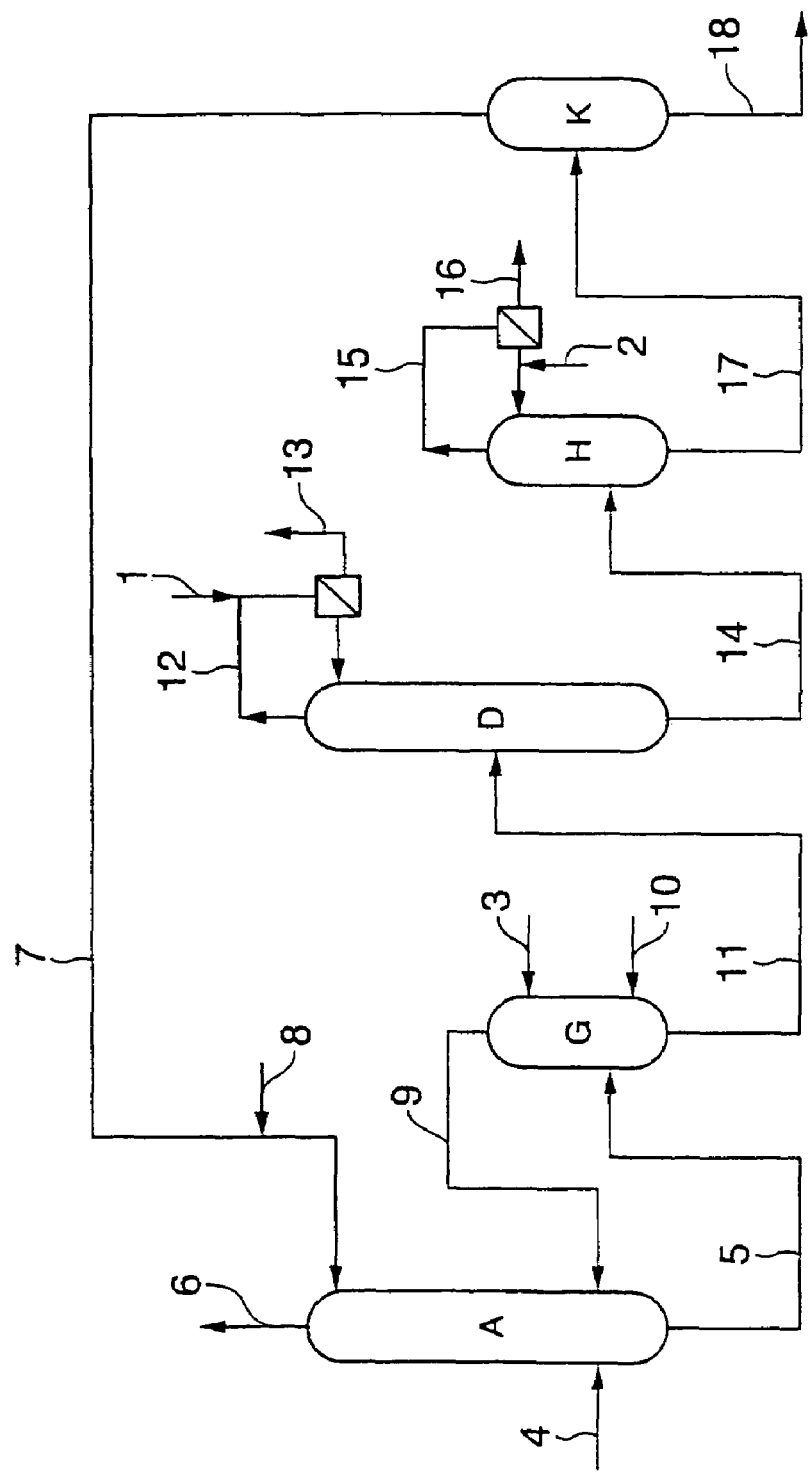
FIG. 3 is a further example of a flow diagram showing a process for producing acrylic acid from raw propylene.

Next, the process shown in FIG. 3 is explained. In FIG. 3, reference character G represents a stripping column, D is a high-boiling fraction separation column (acrylic acid purification column), H is a high-boiling fraction removal column, and K is a solvent recovery column.

An acrylic acid-containing gas obtained by subjecting propylene and/or acrolein to catalytic gas-phase oxidation using a molecular oxygen-containing gas, is introduced into an acrylic acid collection column A through a line 4 and contacted therein with a solvent to obtain an acrylic acid-containing solution.

Then, the thus obtained acrylic acid-containing solution is fed to the stripping column G. The stripping column G is supplied with a gas (gas present in a line 6 which is discharged from a top of the acrylic acid collection column A, or gas obtained after oxidizing and then removing organic substances contained in the gas present in the line 6, etc.) through a line 10 to distil out water and acetic acid from a top thereof and obtain acrylic acid containing the solvent from a bottom thereof. Water and acetic acid distilled out from the top of the stripping column G are introduced into the acrylic acid collection column A, and finally discharged from the top of the acrylic acid collection column A. The acrylic acid discharged from the bottom of the stripping column G through a line 11 is introduced into the high-boiling fraction separation column (acrylic acid purification column) D in order to obtain a high-purity acrylic acid. In the high-boiling fraction separation column D, the obtained high-boiling substances are separated and removed therefrom through a line 14, and a high-purity acrylic acid can be obtained through a line 13. Specific examples of the high-boiling substances discharged through the line 14 may include maleic anhydride, benzaldehyde or the like. These high-boiling substances are introduced into the high-boiling fraction removal column H, and discharged therefrom through a line 16. The solvent separated in the high-boiling fraction removal column H is introduced into the solvent recovery column K through a line 17, and the thus recovered solvent is circulated from a top thereof through a line 7 to the acrylic acid collection column A. In this case, a part or majority of the solvent may be returned from the line 17 directly through the line 7 to the acrylic acid collection column A (not shown). The still higher-boiling substances are separated and removed from a bottom of the solvent recovery column K through a line 18. A liquid containing a polymerization inhibitor may be fed from one or two or more of the lines 1 to 3.

Figure 4:
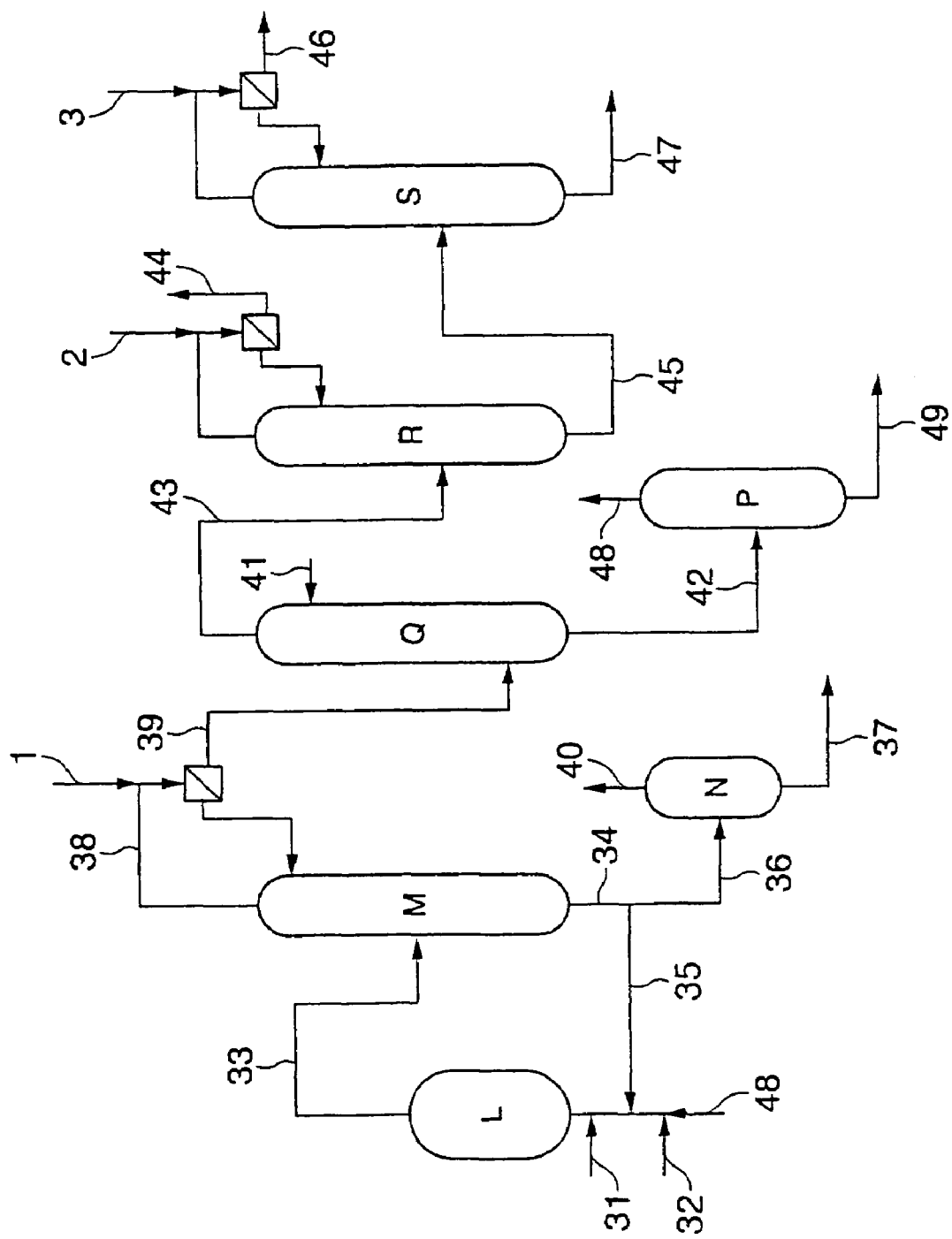
FIG. 4 is an example of a flow diagram showing a process for producing an acrylic ester.

Next, the process shown in FIG. 4 is explained. In FIG. 4, reference character L represents an esterification reactor, M is an acrylic acid separation column, N is a high-boiling fraction decomposition reactor, Q is an alcohol extraction column, P is an alcohol recovery column, R is a low-boiling fraction separation column, and S is an ester purification column.

The esterification reactor L is supplied with acrylic acid, alcohol, circulated acrylic acid and circulated alcohol through lines 31, 32, 35 and 48, respectively. The esterification reactor L is filled with a catalyst such as strong-acid ion exchange resins. The esterification reaction mixture composed of produced ester, unreacted acrylic acid, unreacted alcohol and produced water is discharged from the esterification reactor L through a line 33, and fed to the acrylic acid separation column M. A substantially whole amount of a bottom liquid of the acrylic acid separation column M is discharged therefrom and fed as a circulating liquid through a line 35 to the esterification reactor L.

A part of the bottom liquid of the acrylic acid separation column M is fed to the high-boiling fraction decomposition reactor N through a line 36, and the obtained useful decomposition products are circulated to the process through a line 40. The position to which the useful decomposition products are circulated, may vary depending upon process conditions used. The high-boiling impurities such as polymers separated in the high-boiling fraction decomposition reactor N are removed out of the system through a line 37. Also, the produced ester, unreacted alcohol and produced water are distilled out from a top of the acrylic acid separation column M through a line 38, and a part thereof is circulated as a reflux liquid to the acrylic acid separation column M, and a remaining part thereof is fed to the extraction column Q through a line 39.

Water for extraction of alcohol is fed to the extraction column Q through a line 41, and water containing the recovered alcohol is fed to the alcohol recovery column P through a line 42. The thus recovered alcohol is circulated to the esterification reactor L through a line 48. Water separated in the alcohol recovery column P is discharged through a line 49, and a part or whole of the separated water is circulated as an alcohol-extracting water through the line 41.

The crude acrylic ester obtained in the extraction column Q is fed to the low-boiling fraction separation column R through a line 43. The low-boiling substances containing the acrylic ester are discharged from the low-boiling fraction separation column R though a line 44, and circulated to the process. The position to which the low-boiling substances containing the acrylic ester are circulated may vary depending upon process conditions used. The crude acrylic ester from which the low-boiling substances are removed, is fed to the ester purification column S for producing acrylic ester products, through a line 45, thereby obtaining a high-purity acrylic ester from a top thereof through a line 46. A liquid containing a slight amount of high-boiling substances is discharged from a bottom of the ester purification column S through a line 47, and circulated to the process. The position to which the liquid containing a slight amount of high-boiling substances are circulated may vary depending upon process conditions used.

In this process, a liquid containing a polymerization inhibitor may be fed from one or two or more of the lines 1 to 3.

Figure 5:
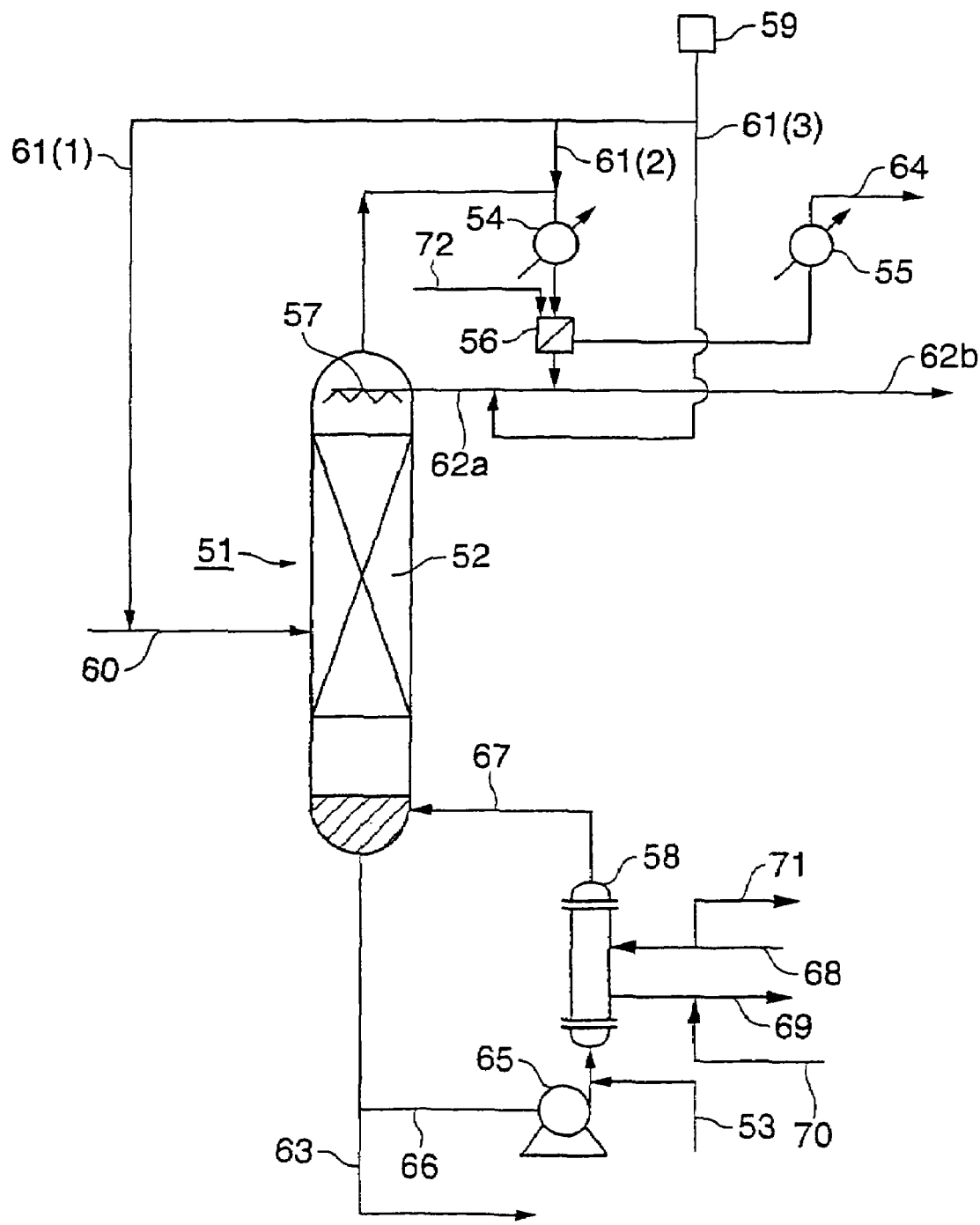
FIG. 5 is a view showing an example of an arrangement including a distillation column for production of crude acrylic monomer and equipments attached thereto.

The distillation column used for distilling crude acrylic monomer and equipments attached thereto as shown in FIG. 5 are explained below. In FIG. 5, reference numeral 51 represents a distillation column, 52 is a packing material layer, a distillation column tray or a packing material, 53 is an inhibitor air feed line, 54 is a heat exchanger for cooling a top gas, 55 is a heat exchanger for cooling a vent gas, 56 is a reflux tank, 57 is a distributor, 58 is a reboiler (heat exchanger for heating), 59 is a polymerization inhibitor-containing liquid tank, 60 is a feed line for acrylic monomer (as a raw material), 61(1) to 61(3) are feed lines for polymerization inhibitor, 62a is a reflux line, 62b is a discharge line for top liquid, 63 is a discharge line for bottom liquid, 64 is an exhaust line for vent gas, 65 is a pump, 66 and 67 are circulation lines for bottom liquid, 68 is a feed line for heating medium, 69 is a delivery line for heating medium, 70 is a feed line for cooling medium, 71 is a delivery line for cooling medium, and 72 is a feed line for inert gas.

A polymerization inhibitor-containing liquid may be fed from one or two or more of the lines 61(1), 61(2) and 61(3). The inhibitor air feed line 53 may be provided at a plurality of positions in various portions of the distillation column.

The distillation column used in the present invention includes all types of distillation apparatuses capable of subjecting the acrylic monomer to gas-liquid equilibrium, and means an apparatus for performing operations such as separation, concentration, recovery and purification thereof. For example, such an apparatus includes the dehydration column B, the low-boiling fraction separation column (acetic acid separation column) C and the high-boiling fraction separation column (acrylic acid purification column) D as shown in FIG. 1; the stripping column G, the high-boiling fraction separation column (acrylic acid purification column) D, the high-boiling fraction removal column H and the solvent recovery column K as shown in FIG. 3; the acrylic acid separation column M, the alcohol recovery column P, the low-boiling fraction separation column R and the ester purification column S as shown in FIG. 4; and the distillation column 51 as shown in FIG. 5.

The distillation column usable in the present invention may be of various types such as a perforated plate tower type, a bubble-cap tower type, a packed tower type and combinations of these types (for example, combination of a perforated plate tower and a packed tower as shown in FIG. 5) irrespective of provision of overflow weirs or down corners. Specific examples of the tray provided in the distillation column may include a bubble-cap tray, a perforate plate tray, a bubble tray, a super-flash tray, a maxflux tray, a dual tray or the like.

Examples of the packing material preferably used in the present invention may include conventional packing materials having various shapes such as a cylindrical shape, a hollow cylindrical shape, a saddle shape, a spherical shape, a cubic shape and a prismatic shape as well as recently commercially available regular or irregular high-performance packing materials having specific shapes.

Examples of these commercially available regular packing materials may include gauze-type regular packing materials such as "SULZER PACKING" produced by Sulzer Brothers Limited, "SUMITOMO SULZER PACKING" produced by Sumitomo Jukikai Kogyo Co., Ltd., "TECHNO-PACK" produced by Mitsui Bussan Co., Ltd., and "M.C. PACK" produced by Mitsubishi Kagaku Engineering Co., Ltd.; sheet-type regular packing materials such as "MELA-PACK" produced by Sumitomo Jukikai Kogyo Co., Ltd., "TECHNOPACK" produced by Mitsui Bussan Co., Ltd., and "M.C. PACK" produced by Mitsubishi Kagaku Engineering Co., Ltd.; grid-type regular packing materials such as "FLEXI-GRID" produced by Cork Inc.; as well as "JEMPACK" produced by Grich Inc., "MONTZPACK" produced by Montz Inc., "GOODROLL PACK" produced by Tokyo Special Wire Netting Co. Ltd., "HONEYCOMB PACK" produced by Nihon Gaishi Co., Ltd., "IMPULSE PACKING" produced by Nagaoka Co., Ltd., or the like.

Examples of the commercially available irregular packing materials may include Rashig ring, "Po-Ring" produced by BASF AG, "Cascade Mini-Ring" produced by Mass-Transfer Inc., "IMTP" produced by Norton Inc., "INTERLOCKS SADDLE" produced by Norton Inc., "TERALET" produced by Nittetsu Kakoki Co., Ltd., "FLEXI-RING" produced by Nikki Co., Ltd., or the like.

The polymerization inhibitor used in the present invention generally includes stable radical substances, or substances capable of forming or readily forming stable radicals by adding to radicals, and may be occasionally referred to as a polymerization suppressor, polymerization prohibitor, a polymerization terminator, a polymerization velocity-reducing agent, etc. In the present invention, all these agents are totally called the "polymerization inhibitor".

Examples of the polymerization inhibitor may include phenol compounds such as hydroquinone, methoxy hydroquinone (methoquinone), pyrogallol, catechol and resorcin; N-oxyl compounds such as tert-butyl nitroxide, 2,2,6,6-tetramethyl-4-hydroxypiperidyl-1-oxyl, 2,2,6,6-tetramethylpiperidyl-1-oxyl, 2,2,6,6-tetramethylpiperidino-oxyl, 4-hydroxy-2,2,6,6-tetramethylpiperidino-oxyl and 4,4',4''-tris-(2,2,6,6-tetramethylpiperidino-oxyl)phosphite; phenothiazine compounds such as phenothiazine, bis-α-methylbenzyl) phenothiazine, 3,7-dioctyl phenothiazine and bis-(α,α'-dimethylbenzyl)phenothiazine; copper-based compounds such as cupric chloride, copper acetate, copper carbonate, copper acrylate, copper dimethyldithiocarbamate, copper diethyldithiocarbamate, copper dibutyldithiocarbamate and copper salicylate; manganese salt compounds such as manganese acetate; phenylenediamines such as p-phenylenediamine; nitroso compounds such as N-nitrosodiphenylamine; ureas such as urea; or thioureas such as thiourea. These compounds may be used singly or in combination of any two or more thereof. Among these polymerization inhibitors, phenothiazine and/or N-oxyl compounds are especially preferred from the standpoints of good polymerization inhibiting effect, anti-corrosiveness of the distillation apparatus and facilitated treatment of waste water discharged from the distillation apparatus.

<Aspect (I) of the Invention>

The feature of the present invention lies in that in stopping and starting operations of a distillation column for producing (meth)acrylic acids, upon stopping an operation of the distillation column, the heating of a reboiler attached to the distillation column is interrupted, and then the reboiler is rapidly cooled; and/or upon initiating the operation for production of the (meth)acrylic acids, an inner wall surface of the distillation column is heated to a temperature higher than a condensation temperature of the (meth)acrylic acids, and the operation of the distillation column is started under the heated condition. The details of the aspect (I) of the present invention will become apparent from the below-mentioned explanations of the other aspects of the present invention.

<Aspect (II) of the Invention>

The important feature of the aspect (II) of the present invention lies in that before starting the operation of the distillation column, the inner wall surface of the distillation column is previously heated to a temperature higher than a condensation temperature of the acrylic monomer. The heating method is not particularly restricted. For example, the heating may be performed by an external heating method of covering a body of the distillation column with a heatable trace member, and then feeding a heat source such as electric current, steam and warm water thereto, or an internal heating method of feeding a heated gas or a heated liquid into the distillation column. The heated gas may be fed from a bottom or a raw material feed section of the distillation column. As the heated gas, there may be used air, nitrogen, carbon dioxide, argon or the like. These gases may be used singly or in the form of a mixture of any two or more thereof. The heated liquid may be sprayed or flowed down from a top of the distillation column through a distributor such as a liquid dispersing device and a liquid dispersion nozzle. Also, the heated gas can be flowed upward from the bottom of the distillation column while allowing the heated liquid to flow down.

In the case where such a process of subjecting propylene or isobutylene to gas-phase catalytic oxidation, absorbing the oxidation reaction mixture into water, and then concentrating the resultant aqueous solution of (meth)acrylic acid in the presence of an azeotropic agent, is conducted as a preliminary step before the process according to the present invention, the azeotropic agent may be subsequently used as the heating medium in the process of the present invention. The use of the azeotropic agent as the heating medium is preferable because there is no risk that specific impurities are mixed therein. Further, the bottom liquid of the distillation column obtained before stopping the operation thereof may also be suitably used as the heating medium.

The inner wall surface of the distillation column may be heated to a temperature higher than a condensation temperature of a gas within the column containing the (meth)acrylic acids under normal operation conditions of the distillation column. The heating temperature is higher by usually 1 to 60° C., preferably 3 to 60° C., more preferably 3 to 40° C. than the condensation temperature. When the heating temperature is less than the above-specified range, there may be caused such a risk that the gases are locally condensed, resulting in production of polymers. When the heating temperature is more than the above-specified range, the polymerization of the acrylic monomer may be induced, or such a high temperature may lead to uneconomical use of the heat source.

The "temperature higher than a condensation temperature of a gas within the column containing the (meth)acrylic acids under normal operation conditions of the distillation column" used herein means, for example, a temperature higher than a condensation temperature of an acrylic acid-containing gas within the column in the case of the distillation column in which acrylic acid is obtained as a top component, or a temperature higher than a condensation temperature of a butyl acrylate-containing gas within the column in the case of the distillation column in which butyl acrylate is obtained as a top component. When two or more acrylic monomers are present in the form of a mixed gas, it is required to adopt as the heating temperature, a temperature higher than a higher one of the two condensation temperatures. Upon actual operation, since the raw liquid to be distilled is not a pure acrylic monomer, but may frequently contain various high-boiling impurities, the condensation temperature of the raw liquid tends to shift to a higher-temperature side. Therefore, as described above, it is preferable to set the heating temperature to a temperature higher by 3 to 60° C. than the condensation temperature of the gas within the column.

In the internal heating method in which the heating medium is fed into the distillation column, since whole portions of the distillation column including the inner wall surface, trays and packing materials can be heated to a uniform temperature, it is sufficient to measure only the temperature of the inner wall surface and control the temperature so as to exceed the above condensation temperature. However, in the external heating method, the temperature of the packing materials tends to become lower than that of the inner wall surface depending upon heating manner, heating time, etc. In such a case, it is preferable to set the temperature of the packing materials to a temperature higher than the above condensation temperature.

In the present invention, it is important that after the inner wall surface of the distillation column is heated, the operation of the distillation column is started while the inner wall surface is kept in the heated state. The operation of the distillation column may be started by successively feeding the raw material (crude acrylic monomer) and the heat source to the reboiler. Before or after feeding the heat source, the raw material may be fed from the raw material feed section, and the amount of the raw material fed may be gradually increased to allow the operation of the distillation column to migrate to normal operation conditions. In the case where the operation of the distillation column is started by the external heating method, the method of heating the inner wall surface of the distillation column after migrating to the normal operation conditions is not particularly restricted. The external heating may be continued, or may be interrupted so as to change to only heating by the heat source from the reboiler.

The distillation procedure according to the present invention may be performed by either continuous distillation or batch distillation. The distillation operation conditions is not particularly restricted, and may be appropriately selected in view of type of the distillation column, shape of the packing material, kinds and contents of impurities contained in the crude acrylic monomer. The distillation procedure may be performed at a column top temperature of usually 20 to 80° C., preferably 40 to 60° C. and a column bottom temperature of usually 60 to 120° C., preferably 65 to 110° C. under a column top pressure of usually about 0.7 to 106 kPa.

The crude acrylic monomer is preferably distilled in the presence of the polymerization inhibitor. The polymerization inhibitor and the crude acrylic monomer as a raw material may be fed in the form of a mixture thereof to the distillation column. Alternatively, the polymerization inhibitor and the crude acrylic monomer may be separately fed to the distillation column, or the polymerization inhibitor may be fed to the reflux tank and then sprayed or flowed down in the distillation column from the top thereof through a distributor (such as a liquid dispersing device and a liquid dispersion nozzle). The polymerization inhibitor may be usually used in the form of an aqueous solution, an aqueous solution slurry, an organic solvent-based solution or an organic solvent-based slurry. As the organic solvent, there may be used alcohols such as methanol, ethanol and butyl alcohol; ketones such as acetone, methyl ethyl ketone and methyl isobutyl ketone; carboxylic acids such as acetic acid, propionic acid, acrylic acid and methacrylic acid; aromatic hydrocarbons such as benzene, toluene and xylene; esters such as methyl acetate, butyl acetate, methyl acrylate, butyl acrylate, methyl methacrylate and ethyl methacrylate; or the like. The solvents may be used in the form of a mixture of any two or more thereof, for example, a mixture of water and toluene, a mixture of water and (meth)acrylic acid, or crude (meth)acrylic acid containing dimers or trimers of (meth) acrylic acid (bottom liquid of (meth)acrylic acid distillation column). Further, these organic solvents may also be used as the above heating medium.

<Aspect (III) of the Invention>

In the aspect (III) of the present invention, when the operation of the distillation column is stopped by interrupting the supply of the (meth)acrylic acids to be distilled, the heating of the reboiler of the distillation column is interrupted, then the reboiler is rapidly cooled to abruptly reduce the bottom temperature of the distillation column, and thereafter, introducing an inert gas to the distillation column to return the inside pressure of the distillation column to an ordinary pressure.

In the following descriptions, the method for stopping the operation of the distillation column according to the present invention is more concretely explained by referring to FIG. 5 showing an example of the distillation column and equipments attached thereto to which the above method is applied.

As shown in FIG. 5, the distillation column 51 is equipped with the reboiler 58 and the reflux tank 56. The crude acrylic monomer (acrylic acid or acrylic ester) to be distilled is introduced into the distillation column 51 through a line 60. The bottom liquid of the distillation column 51 is removed therefrom through a line 66 provided with a pump 65, and then heated in the reboiler 58 and returned to the bottom of the distillation column 51 through a line 67. The reboiler 58 is connected with a feed line 68 for a heating medium and a delivery line 69 for the heating medium. Further, the delivery line 69 is connected with a feed line 70 for a cooling medium, whereas the feed line 68 for a heating medium is connected with a delivery line 71 for the cooling medium.

In addition, the line 66 for delivering the bottom liquid of the distillation column 51 to the reboiler 58, is connected with an inhibitor air feed line 53 for feeding an oxygen-containing gas such as oxygen and air for preventing the polymerization. Reference numeral 63 represents a discharge line for removing the bottom liquid of the distillation column 51.

On the other hand, the fraction distilled out from the top of the distillation column 51 is cooled in a heat exchanger 54 for cooling, and then fed to the reflux tank 56. A part of the top fraction is circulated from the reflux tank 56 to the distillation column 51 through a reflux line 62a, and a remaining part of the top fraction is removed through a line 62b.

The reflux tank 56 is connected with an inert gas feed line 72 for returning the inside pressure of the distillation column to an ordinary pressure. Reference numeral 55 represents a heat exchanger for cooling a vent gas. The vent gas is cooled in the cooling heat exchanger 55, and then discharged through a line 64 by operation of an ejector (not shown).

In the above distillation facility, as the heating medium for heating the reboiler, there may be used either steam or organic heating medium. In the case where an water-based cooling medium is used for rapid cooling of the reboiler, steam is preferably used as the heating medium since the heating medium can be reused as the cooling medium without risk of mixing impurities therein. The temperature of the heating medium is usually 100 to 200° C.

Also, as the cooling medium, there may be used any of water such as typically clean water, industrial water, re-cooled water, boiler water and steam-condensate water, sea water and organic heating medium. At least one of these media may be used as the cooling medium. The temperature of the cooling medium is preferably 0 to 40° C. Although the cooling medium having a temperature of less than 0° C. or more than 40° C. is usable, if the temperature of the cooling medium is less than 0° C., it is required to separately prepare a heating medium, resulting in uneconomical procedure, and if the temperature of the cooling medium is more than 40° C., it is required to increase a heat transfer surface area for rapid cooling, also resulting in uneconomical procedure.

As the inert gas fed for returning the inside pressure of the distillation column to an ordinary pressure, there may be used nitrogen gas, carbon dioxide gas or the like. Of these gasses, the nitrogen gas is preferred because of good availability.

When the operation of the distillation column is stopped according to the present invention, the inside pressure of the distillation column is preferably not more than 16 kPa. If the inside pressure of the distillation column is more than 16 kPa, a combustible gas such as acrylic acid may be fallen within its explosion range during the stopping operation and, therefore, is undesirable in view of safety. The inside pressure of the distillation column is more preferably not more than 13 kPa, still more preferably not more than 10 kPa.

The bottom temperature of the distillation column upon the rapid cooling of the reboiler is not more than a boiling point of the cooling medium used for cooling the reboiler. Since water such as re-cooled water is usually used as the cooling medium for the reboiler, the bottom temperature of the distillation column upon the rapid cooling of the reboiler is preferably not more than 100° C.

Further, the bottom temperature of the distillation column after the rapid cooling of the reboiler is preferably not more than 50° C. If the bottom temperature of the distillation column after the rapid cooling of the reboiler is more than 50° C., a vapor of acrylic acid or the like tends to be polymerized when exposed to the inert gas atmosphere, and may be fallen within its explosion range when exposed to air upon feeding the vapor to any tank after returning the inside pressure of the distillation column to an ordinary pressure. The rapid cooling temperature of the reboiler is preferably not more than 50° C., more preferably 30 to 40° C.

Meanwhile, the rapid cooling operation used in the present invention means an operation for reducing the bottom temperature of the distillation column for a short period of time, for example, such an operation that the bottom temperature of the distillation column is reduced by not less than 50° C. for 360 minutes, namely such a cooling operation conducted at a cooling velocity of not less than 0.15° C./minute. More specifically, the rapid cooling operation is performed such that after initiating the stopping operation for the distillation column, namely after interrupting the supply of the heating medium to the reboiler, the bottom temperature of the distillation column is reduced to not more than 50° C., preferably 30 to 40° C. within 360 minutes, preferably for 150 to 300 minutes.

Specific steps of the process for stopping the operation of the distillation column according to the present invention are explained below by referring to the case where the operation of the distillation column 51 shown in FIG. 5 is stopped.

Step 1: Interrupting supply of the heating medium to the reboiler 58 through the line 68.

Step 2: Interrupting supply of the crude acrylic monomer from the line 60 while continuing the reflux from the line 62a, and also interrupting removal of the top liquid through the line 62b.

Step 3: Feeding the cooling medium to the reboiler 58 through the line 70 to rapidly cool the reboiler 58, whereupon the bottom liquid of the distillation column 51 is rapidly cooled to a temperature of 40 to 50° C. while continuously operating the pump 65.

Step 4: Interrupting stream trace-heating. Namely, upon distillation of acrylic acids, since the steam trace-heating is usually provided in order to prevent vapors of the acrylic acids from being condensed on an inner surface of the distillation column by the influence of outside air, such a steam trace-heating should be interrupted.

Step 5: Immediately after initiating the rapid cooling operation of the step 3, refluxing a whole amount of the liquid in the reflux tank 56 to the distillation column 51. Specifically, the amount of the liquid refluxed from the reflux tank 56 to the distillation column 51 is increased without interrupting the reflux usually conducted during the operation of the distillation column. Alternatively, by interrupting the removal of the liquid in the reflux tank 56 out of the system, a whole amount of the liquid that is evaporated from the distillation column 51, cooled and condensed by the cooling heat exchanger 54 and then introduced into the reflux tank 56 is circulated into the distillation column 51.

Step 6: Interrupting supply of the polymerization inhibitor.

Step 7: Interrupting supply of the inhibitor air from the line 53.

Step 8: Stopping the operation of the ejector (not shown) and closing a valve provided on a vacuum line.

Step 9: Feeding the inert gas such as nitrogen to the reflux tank 56 through the line 72 to release the reduced pressure condition and return the inside pressure of the distillation column 51 to an ordinary pressure.

<Aspects (IV) and (V) of the Invention>

The important feature of the aspects (IV) and (V) of the present invention lies in that polymers adhered and deposited within the distillation column after operating the distillation column for a predetermined period of time are cleaned or washed out by a three stage washing process, preferably a four stage washing process.

(1) Water washing:

The distillation column is first washed with water. The water-washing step is required to wash and flow down useful substances (e.g., acrylic acid or acrylic ester) remaining within the distillation column to the bottom thereof in order to recover the useful substances. The washing liquid recovered from the bottom of the distillation column is transferred into the tank and stored therein. After the distillation operation is re-started, the thus recovered washing liquid is circulated and fed to an appropriate position within the process (e.g., the dehydration column (B) shown in FIG. 1) in view of composition of the washing liquid. If the aqueous alkali washing step is first conducted by omitting the water-washing step, the (meth)acrylic acids tend to undergo polymerization by heat of neutralization between the acid and alkali. Therefore, it is possibly required to remove the (meth)acrylic acids out of the system. The water-washing operation may be conducted only one time, or may be repeated several times. For example, the water-washing step may be preferably performed by three divided washing operations in which the washing liquids obtained from the first and second washing operations are recovered as useful substances, whereas the washing liquid obtained from the third washing operation is fed to a waste water treatment step, from economical viewpoint.

(2) Aqueous alkali washing:

As the aqueous alkali solution, there may be used aqueous solutions of potassium hydroxide, sodium hydroxide, sodium carbonate or the like. The concentration of the aqueous alkali solution is usually in the range of 1 to 25% by weight. Also, aqueous ammonia can be used as the aqueous alkali solution at a concentration of usually 1 to 25% by weight, preferably 1 to 10% by weight.

The aqueous alkali solution may be first fed to the reflux tank of the distillation column and then to the top of the distillation column through the reflux line, or may be directly fed to the distillation column through the reflux line. The aqueous alkali solution fed to the distillation column is flowed down to the bottom thereof while swelling or dissolving the polymers present within the distillation column. In order to allow the aqueous alkali solution to sufficiently contact with the polymers, inner wall surface and packing materials within the distillation column, the aqueous alkali solution fed from the top of the distillation column and flowed down to the bottom thereof may be repeatedly circulated to the top of the distillation column. In the case where the aqueous alkali solution is repeatedly used for washing, the aqueous alkali solution flowed down to the bottom of the distillation column is preferably passed through a strainer of the pump, etc., to separate and remove solids contained therein before being circulated to the top of the distillation column. The aqueous alkali solution may be fed not only from the top of the distillation column but also from the raw material feed section thereof to supply an additional amount of the aqueous alkali solution.

In the case where the packed column is provided at an upper portion thereof with the distributor (liquid dispersing device or liquid dispersion nozzle), the aqueous alkali solution is preferably fed through the distributor.

The aqueous alkali washing may be conducted at a temperature of usually 10 to 100° C. for usually 30 to 360 minutes. The amount of the aqueous alkali solution fed may vary depending upon the degrees of clogging and contamination within the distillation column, and is usually about 0.5 to 5 $m^3$/hr per 1 $m^2$ of a cross section of the distillation column (or cumulative amount thereof when the aqueous alkali solution is repeatedly used).

(3) Organic solvent washing:

In the present invention, subsequent to the aqueous alkali washing, the distillation column is washed with an organic solvent. The organic solvent washing step is performed mainly for the purposes of removing alkali components, polymers, and decomposed products thereof and impurities, and drying the inside of the distillation column. Examples of the organic solvent may include alcohols such as methanol, ethanol and butyl alcohol; ketones such as acetone, methyl ethyl ketone and methyl isobutyl ketone; carboxylic acids such as acetic acid, propionic acid, acrylic acid and methacrylic acid; aromatic hydrocarbons such as benzene, toluene and xylene; saturated hydrocarbons such as hexane, heptane, octane, nonane and decane; cyclic hydrocarbons such as cyclohexane and cyclopentane; esters such as methyl acetate, butyl acetate, methyl acrylate, butyl acrylate, methyl methacrylate and ethyl methacrylate; aldehydes such as propionaldehyde and benzaldehyde; or mixtures thereof.

Since the washing liquid obtained from the organic solvent washing step contains various components, the washing liquid may be usually preserved in a storage tank for off-specification products, and then the organic solvent may be recovered from the distillation column within the process during a normal operation thereof. Also, according to the kind of organic solvent used, the distillation column washed with the organic solvent may be directly used for the distillation for recovering useful substances, and in some cases, the organic solvent may be incinerated therein.

In the present invention, as the organic solvent, there may be efficiently used not only high-purity organic solvents as described above, but also various organic solvent-based substances obtained from the processes conducted before or after the distillation column. Examples of the organic solvent-based substances usable in the present invention may include the azeotropic agent used for concentrating the aqueous solution containing the (meth)acrylic acids, the crude (meth)acrylic acids obtained from the concentration step, the purified (meth)acrylic acids (products) obtained before stopping the operation of the distillation column, the bottom liquid of the distillation column obtained before stopping the operation of the distillation column, off-specification products recovered upon stopping the operation of the plant, similar product liquids before product inspection, off-specification products after product inspection, or the like.

The amount of water contained in the organic solvent is controlled to preferably not more than 2% by weight, more preferably not more than 1% by weight in consideration of excellent dehydration efficiency. The washing temperature is preferably 0 to 95° C. The method of feeding the organic solvent is the same as that used for the aqueous alkali washing.

(2a) Water washing:

In the present invention, there may be used a four-stage washing process in which an additional water washing step (2a) is interposed between the aqueous alkali washing (2) and the organic solvent washing (3). The method of feeding water and the washing conditions used in the water-washing step (2a) are substantially the same as those used in the water washing step (1). Although the water may be fed together with small amounts of inorganic acids, surfactants or the like, it is preferable to use a pure water at a final stage of the water washing step (2a) because these substances remaining in the distillation column may produce adverse influences. The addition of the water washing step (2a) has such a merit that the alkali components are removed from the washing liquid obtained in the organic solvent washing step, thereby facilitating the treatment of the washing liquid. More specifically, the washing liquid obtained upon conducting the organic solvent washing step immediately after the aqueous alkali washing step, contains residual alkali, so that troubles of polymerization tend to be caused. However, when the water washing step (2a) is interposed between these steps, the occurrence of polymerization by the residual alkali can be inhibited.

In the above three-stage or four-stage washing procedure, a small amount of a polymerization inhibitor may be fed especially upon the organic solvent washing step. For example, the addition of the polymerization inhibitor is effective when the organic solvent contains the (meth)acrylic acids. The kinds of the polymerization inhibitors usable in the washing step are the same as described above.

After completion of the washing procedure, the distillation operation is re-started. The distillation operation may be in the form of either continuous distillation or batch distillation. The distillation operation conditions are not particularly restricted, and may be appropriately determined in consideration of kinds and contents of impurities contained in the crude (meth)acrylic acids. The distillation operation may be conducted at a column top temperature of usually 20 to 80° C. and a column bottom temperature of usually 60 to 120° C. under a column top pressure of usually about 0.7 to 106 kPa.

<Aspect (VI) of the Invention>

The important feature of the aspect (VI) of the present invention lies in that prior to starting the operation of the distillation column, the inner wall surface of the distillation column is previously wetted with the polymerization inhibitor. As described above, the polymerization inhibitor is in a liquid or solid state at an ordinary temperature. However, since the polymerization inhibitor can prevent polymerization of the acrylic monomer even when used in a small amount, the polymerization inhibitor is not used singly in itself, but rather used in the form of a solution or slurry in a liquid medium.

As the liquid medium, there may be used water and organic solvents. Examples of the organic solvents may include alcohols such as methanol, ethanol and butyl alcohol; ketones such as acetone, methyl ethyl ketone and methyl isobutyl ketone; carboxylic acids such as acetic acid, propionic acid, acrylic acid and methacrylic acid; aromatic hydrocarbons such as benzene, toluene and xylene; esters such as methyl acetate, butyl acetate, methyl acrylate, butyl acrylate, methyl methacrylate and ethyl methacrylate; or the like. These organic solvents may be used in the form of a mixture of any two or more thereof, for example, a mixture of water and toluene, a mixture of water and acrylic acid, and crude acrylic acid containing dimers or trimers of acrylic acid (bottom liquid of the acrylic acid distillation column).

In the case where such a process of subjecting propylene or isobutylene to gas-phase catalytic oxidation, absorbing the resultant oxidation reaction mixture in water, and then concentrating the obtained aqueous solution of acrylic acid or methacrylic acid in the presence of an azeotropic agent is present as a preliminary stage before conducting the process of the present invention, the azeotropic agent may be is suitably directly used as the liquid medium for the polymerization inhibitor. In addition, a bottom liquid of the concentration column may also be suitably used as the liquid medium. Thus, in the case where the solvent or the solution used in the processes conducted before or after the process of the present invention is used as the liquid medium for dissolving the polymerization inhibitor, impurity components can be effectively prevented from being mixed therein.

Among the above organic solvents, alcohols, ketones and aromatic hydrocarbons may be preferably used as the azeotropic agent.

The concentration of the solution of the polymerization inhibitor is usually not more than 3 times, preferably not more than 2 times a saturation solubility thereof. The polymerization inhibitor remains undissolved in the liquid medium when used at a concentration higher than the saturation solubility. However, the polymerization inhibitor remaining within the distillation column causes no significant problem because the residual polymerization inhibitor can be dissolved in the liquid within the distillation column during a normal operation thereof.

The method of wetting the inner wall surface of the distillation column with the polymerization inhibitor-containing liquid is not restricted. The "inner wall surface of the distillation column" used herein includes, in addition to a vertical inner wall surface thereof, trays for perforated plate distillation columns, packing materials for packed columns, and both trays and packing materials for combined type distillation columns.

The inner wall surface of the distillation column may be wetted by the method of feeding the polymerization inhibitor-containing liquid to the reflux tank of the distillation column, and then feeding the liquid to the top of the distillation column through the reflux line. In order to sufficiently wet the inner wall surface of the distillation column, the polymerization inhibitor-containing liquid which is fed from the top thereof and dropped onto the bottom thereof, is repeatedly circulated to the top of the distillation column. Further, the polymerization inhibitor-containing liquid may be additionally fed from the raw material feed section in addition to the feeding from the top thereof.

In the case where the distributor (liquid dispersing device or liquid dispersion nozzle) is mounted at the top of the packed column, the polymerization inhibitor-containing liquid is preferably fed through the distributor to more uniformly feed the liquid into the distillation column.

The percentage of a wetted area of the inner wall surface of the distillation column is ideally 100%, but is not necessarily required to be 100% according to the present inventors' knowledge. In practice, it has been confirmed that a sufficient wetting effect has been attained only by allowing the liquid fed from the reflux tank or the distributor to drop through the distillation column, and there have been obtained such small-scale experimental data that the percentage of a wetted area of the inner wall surface reaches about 50 to 100% by the dropping. From these facts, it is suggested that the percentage of wetted area capable of exhibiting a good wetting effect is about 20% or more. Therefore, the percentage of wetted area of the inner wall surface of the distillation column may be actually selected from the range of not less than 20%, preferably not less than 40%, more preferably 50 to 100%.

The wetting conditions of the inner wall surface, packing materials and trays of the distillation column may be readily observed through an inspection window (fitted with pressure-tight glass), if required. Once the wetting conditions are determined, it is not particularly required to observe the inside of the distillation column, i.e., the provision of such an inspection window is not necessarily required. The wetting conditions may be experimentally set while stopping the operation of the distillation column.

In the present invention, after the inner wall surface of the distillation column is wetted with the polymerization inhibitor-containing liquid, the operation of the distillation column is started. In the most preferred embodiment of the present invention, after wetting, the operation of the distillation column is started while keeping the inner wall surface in the wetted state. In the methods of flowing down or spraying the polymerization inhibitor-containing liquid, it will take a certain period of time until the liquid is reached to or reaches a major part of the inner wall surface of the distillation column. On the other hand, when a too long time elapses after wetting the inner wall surface of the distillation column, the liquid is evaporated so that the inner wall surface is dried up. Even when dried up, the non-volatile polymerization inhibitor is still held on the inner wall surface of the distillation column in a coating-like state, and can exhibit its inherent effect.

In the case where a vapor of the acrylic monomer is condensed on the inner wall surface of the distillation column to form a liquid, the polymerization inhibitor is preferably immediately dissolved in the liquid. In order to enhance a dissolving velocity of the polymerization inhibitor in the liquid, the wetting condition is kept so as not to excessively dry up the inner wall surface. The degree of evaporation of the liquid component varies depending upon kind of polymerization inhibitor-containing liquid and atmosphere within the distillation column (operation conditions of the distillation column). The operation of the distillation column may be started usually within 12 hours, preferably within 6 hours after the inner wall surface thereof is wetted. This allows the inner wall surface to be kept in a fully or almost fully wetted state, so that the polymerization inhibitor can be suitably dissolved therein. The operation of the distillation column may be started merely by feeding the raw material (crude acrylic monomer) to the reboiler and successively supplying the heat source to the reboiler. Before or after supplying the heat source, the raw material may be fed from the raw material feed section, and the amount of the raw material fed may be gradually increased so as to migrate to a normal operation condition of the distillation column.

The distillation procedure according to the present invention may be conducted in the form of either continuous distillation or batch distillation. The distillation operation conditions are not particularly restricted, and may be appropriately determined in consideration of kinds and contents of impurities contained in the acrylic monomer, etc.

Respective steps for performing the process of the present invention are explained below by referring to FIG. 5.

Step 1: Feeding a liquid medium to the reflux tank 56;

Step 2: Feeding the liquid medium of Step 1 together with a liquid fed from the polymerization inhibitor-containing liquid tank 59 to the distributor 57 through the line 61(3) and then the reflux line 62a;

Step 3: Dispersing or spraying the polymerization inhibitor-containing liquid into a top of the distillation column from the distributor 57;

Step 4: Initiating a cooling operation using the top gas-cooling heat exchanger 54 and the vent gas-cooling heat exchanger 55;

Step 5: Allowing the polymerization inhibitor-containing liquid to flow down through a packing material layer and/or a perforated plate layer 52 while wetting the inner wall surface of the distillation column, and then accumulating the liquid on the bottom thereof;

Thereafter, the following steps 6-1 and/or 6-2 are conducted.

Step 6-1: Continuing the above Step 5 for a predetermined period of time to sufficiently wet the inner wall surface of the distillation column;

Step 6-2: after Step 5, feeding and circulating the liquid accumulated on the bottom of the distillation column into the distillation column through the line 60, and continuing this procedure for a predetermined period of time to sufficiently wet the inner wall surface of the distillation column;

Step 7: Feeding the acrylic monomer (raw material) containing the polymerization inhibitor into the distillation column through the line 60, and accumulating a predetermined amount of the raw material in the reboiler of the distillation column;

Step 8: Feeding the heat source to the reboiler-heating heat exchanger 58 to start the operation of the distillation column; and Step 9: Initiating the reflux of the liquid from the reflux tank 56 to establish mass balance between the feed line 60 and the lines 62b, 63 and 64 and allow the distillation column to shift to its normal operation.

<Aspect (VII) of the Invention>

In the aspect (VII) of the present invention, the handling steps (handling devices) for (meth)acrylic acid, for example, in the above production process, may include the absorption step (absorption column), the concentration step (dehydration distillation column), and the purification step (distillation column). Also, the handling steps (handling devices) for (meth)acrylic ester, may include the purification step (distillation column), etc. The handling devices may also include equipments attached to these devices such as condenser, reboiler, strainer, pump and connecting conduits as well as storage tank.

The volatile base substance used in the present invention means such a base substance that is kept in a gaseous state at an ordinary temperature (25° C.) under atmospheric pressure. Examples of the volatile base substance may include, in addition to typical ammonia, methylamine (boiling point: −6.3° C.), ethylamine (boiling point: 16.6° C.) or the like. Among these substances, ammonia is suitably used from the standpoints of weak base and inexpensiveness.

The method of removing solids derived from polymerizable compounds adhered onto the surface of the handling devices, may vary depending upon kinds of handling devices used. For example, in the case of the handling devices having a simple structure such as conduits, there may be adopted a method of flowing the volatile base substance (gas) therethrough and then flowing a wash water therethrough, a method of flowing an aqueous solution of the volatile base substance therethrough, or the like. By using such a volatile base substance having a weak alkalinity, the polymerizable compounds adhered onto the surface of the handling devices may be converted into swelled solids that have a low viscosity and are peelable therefrom in dried-up state.

The washing and removing method using the volatile base substance as a washing agent according to the present invention may be suitably applied to removal of solids adhered to such portions to which the conventional aqueous alkali solution is hardly reached (insides of the absorption column and distillation column). The effects of the present invention can be more remarkably exhibited when applied to the above case. The washing and removing method of the present invention is more specifically explained below by referring to the distillation column (plate column) used in the process for production of acrylic acid.

After stopping the operation of the distillation column, even when acrylic acid is removed therefrom, a small amount of acrylic acid is still adhered to the inside of the distillation column. The adhesion of acrylic acid may be caused in any portions within the distillation column, and, in particular, tends to be more frequently caused at portions where the amount of liquid flowed therethrough is relatively small, such as, for example, rear side of respective trays, tray-supporting portions, walls and vicinities thereof.

When the volatile base substance is fed to the distillation column immediately after removal of acrylic acid, there may be caused problems such as increase in amount of polymers produced and curing of the polymers due to heat generated by the acid-base reaction. Therefore, the inside of the distillation column is preferably washed with a solvent before feeding the volatile base substance thereto. Such a washing procedure may be performed by feeding the wash solvent from the top or medium section of the distillation column and simultaneously circulating a part or whole of the bottom liquid to a suitable feed position. In order to inhibit the polymerization within the distillation column, the distillation operation temperature is controlled to usually not more than 80° C., preferably not more than 60° C. As the wash solvent, water may be suitably used.

In the case where the volatile base substance is used in the form of an aqueous solution, as water used for preparation of the aqueous solution, there may be used the above waste wash water. In this case, the amount of the volatile base substance used is increased by an amount capable of neutralizing acrylic acid containing in the waste water. However, the amount of the wash water (discharge amount) is advantageously reduced. The concentration of the volatile base substance is usually 1 to 20% by weight, preferably 2 to 10% by weight.

The aqueous solution of the volatile base substance is fed to the distillation column, and then circulated. Therefore, the aqueous solution of the volatile base substance may be fed to any of the top, medium section and bottom of the distillation column, preferably to the top or medium section thereof. The feed temperature of the aqueous solution of the volatile base substance is usually not more than 60° C. The circulation of the liquid to the top or medium section of the distillation column may be conducted using a circulation pump. The circulation of the liquid enables even the swelled solids adhered to the rear side of respective trays (plates) to be removed therefrom. The thus removed swelled solids are then separated by passing through a strainer provided on the circulation line, if required. When the bottom liquid exhibits neutrality or acidity, the pH value of the liquid is controlled to not less than 9 by adding an additional amount of the volatile base substance thereto. After completion of the washing, the waste washing liquid is removed from the bottom of the distillation column, and residual base within the distillation column is then removed. The method of removing the residual base is not particularly restricted. From the viewpoint of simplicity, there may be suitably used such a method of adding water into the distillation column, refluxing the water, and removing the resultant waste water therefrom, followed by heating.

PREFERRED EMBODIMENT FOR CARRYING OUT THE INVENTION

The present invention is described below in more detail with reference to the following examples, but these examples are only illustrative and not intended to limit the scope of the present invention thereto.

<Regarding Aspect (II) of the Invention>

Example 1

A stainless steel (SUS316) distillation column as shown in FIG. 5 having an inner diameter of 1,100 mm and a length of 20,000 mm, which was filled with an irregular packing material (IMTP) produced by Norton Inc., to form a packing material layer having a height of 14 m therewithin, was used to conduct the distillation of crude acrylic acid. The distillation column was provided around an outer periphery thereof with a steam conduit as a trace line which was covered with a heat insulating material (calcium silicate). Prior to distillation, 120° C. steam was fed through the trace conduit. After about 3 hours, the temperatures of various portions of the distillation column were measured. As a result, it was confirmed that the temperature of an outer wall surface of the distillation column was 118° C., the temperatures of an inner wall surface of the distillation column was 110° C., and the temperature of the packing material filled therein was 93° C.

Next, a mixture containing 98.5% by weight of acrylic acid, 0.3% by weight of maleic acid and 0.3% by weight of an acrylic acid dimer as a crude acrylic monomer was heated to 90° C., and fed to the distillation column at a feed rate of 1300 kg/hr. In addition, a solution prepared by dissolving 8% by weight of methoquinone in acrylic acid and a solution prepared by dissolving 1% by weight of phenothiazine in acrylic acid, were fed from the polymerization inhibitor-containing liquid tank 59 to the distillation column at feed rates of 34 kg/hr and 31 kg/hr, respectively. The distillation column was further supplied with a heat source, and then controlled in inside pressure, etc. After about 5 hours, the operation of the distillation column was stabilized under a top pressure of 2.9 kPa and a bottom pressure of 7.9 kPa at a top temperature of 53° C. and a bottom temperature of 75° C. When a high-purity acrylic acid having a purity of not less than 99.8% by weight was recovered from the top of the distillation column, the operation thereof was stopped to remove a residual liquid present therein and then inspect the inside of the distillation column. As a result, it was confirmed that no solids (polymers) were present within the distillation column and around the packing material.

In this example, since the top pressure was 2.9 kPa, an acrylic acid-containing gas existing at the top of distillation column had a condensation temperature of about 53° C. Thus, it was recognized that the temperature of the inner wall surface of the distillation column which was preheated to 110° C. prior to starting the distillation operation was higher by 57° C. than the condensation temperature at the top thereof, and higher by 35° C. than the condensation temperature at the bottom thereof.

Comparative Example 1

The same procedure as defined in Example 1 was conducted except that the heating of the inside of the distillation column prior to starting the distillation operation was omitted. At the time of starting the distillation operation, the temperature of the outer wall surface of the distillation column, the temperature of the inner wall surface of the distillation column and the temperature of the packing material filled therein all were 25° C., respectively.

The rise of the bottom pressure was observed from the start of the distillation operation. After 5 hours, since the bottom pressure and temperature reached 12 kPa and 86° C., respectively, the operation of the distillation column was stopped, and the inside of the distillation column was observed. As a result, it was recognized that acrylic acid polymers were adhered to a portion of the inner wall surface located above the raw material feed section, as well as the packing material in the vicinity thereof.

Example 2

The same procedure as defined in Example 1 was conducted except that the irregular packing material (IMTP) produced by Norton Inc., was replaced with 21 perforated plates (dual trays). More specifically, the trace conduit was supplied with 120° C. steam. When temperatures of various portions of the distillation column were measured, it was confirmed that the temperature of the outer wall surface of the distillation column was 118° C., the temperature of the inner wall surface of the distillation column was 110° C. and the temperature of the perforated plates fitted therein was 89° C.

Next, the distillation column was further supplied with a mixture having the same composition as that of Example 1 as crude acrylic monomer, and then controlled in inside temperature and pressure, etc. After about 4 hours, the operation of the distillation column was stabilized under a top pressure of 2.8 kPa and a bottom pressure of 9.1 kPa at a top temperature of 53° C. and a bottom temperature of 78° C. When a high-purity acrylic acid having a purity of not less than 99.8% by weight was recovered from the top of the distillation column, the operation thereof was stopped to remove a residual liquid present therein and then inspect the inside of the distillation column. As a result, it was confirmed that no solids (polymers) were recognized within the distillation column and around the packing material.

Comparative Example 2

The same procedure as defined in Example 2 was conducted except that the heating of the inside of the distillation column prior to starting the distillation operation was omitted. At the time of starting the distillation operation, the temperature of the outer wall surface of the distillation column and the temperature of the inner wall surface of the distillation column were 25° C., respectively.

The rise of the bottom pressure was observed from the start of the distillation operation. After 5 hours, since the bottom pressure and temperature reached 11 kPa and 84° C., respectively, the operation of the distillation column was stopped, and then the inside of the distillation column was observed. As a result, it was recognized that acrylic acid polymers were adhered to a portion of the inner wall surface located above the raw material feed section, as well as the perforated plates in the vicinity thereof.

Example 3

A stainless steel (SUS304) distillation column as shown in FIG. 5 having an inner diameter of 1,100 mm and a length of 26,000 mm, which was filled with an irregular packing material (IMTP) produced by Norton Inc., to form a packing material layer having a height of 13 m therein, was used to conduct the distillation of crude ethyl acrylate.

The distillation column was provided around an outer periphery thereof with a steam conduit as a trace line which was covered with a heat insulating material (calcium silicate). Prior to distillation, 120° C. steam was fed through the trace conduit. After about 3 hours, the temperatures of various portions of the distillation column were measured. As a result, it was confirmed that the temperature of an outer wall surface of the distillation column was 118° C., the temperature of an inner wall surface of the distillation column was 110° C. and the temperature of the perforated plates fitted therein was 92° C.

Next, a mixture containing 97.4% by weight of ethyl acrylate, 1.8% by weight of water, 0.4% by weight of acrylic acid, 0.4% by weight of ethanol and 0.1% by weight of ethyl acetate as a crude acrylic monomer was fed to the distillation column at a feed rate of 6,000 kg/hr. In addition, a solution prepared by dissolving 5% by weight of hydroquinone in ethanol, was fed from the polymerization inhibitor-containing liquid tank 59 to the distillation column at a feed rate of 60 kg/hr. The distillation column was further supplied with a heat source, and then controlled in inside pressure, etc. After about 6 hours, the operation of the distillation column was stabilized under a top pressure of 62.7 kPa and a bottom pressure of 69.3 kPa at a top temperature of 76° C. and a bottom temperature of 84° C. When crude ethyl acrylate having a purity of not less than 99.1% by weight was recovered from the top of the distillation column, the operation thereof was stopped to remove a residual liquid present therein and then inspect the inside of the distillation column. As a result, it was confirmed that no solids (polymers) were present within the distillation column and around the packing material.

In this example, the condensation temperature of an ethyl acrylate-containing gas was 76° C. at the top of distillation column, and 84° C. at the bottom thereof. Thus, it was recognized that the temperature of the inner wall surface of the distillation column which was preheated to 110° C. prior to starting the distillation operation was higher by 34° C.

than the condensation temperature at the top thereof, and higher by 26° C. than the condensation temperature at the bottom thereof.

Comparative Example 3

The same procedure as defined in Example 3 was conducted except that the heating of the inside of the distillation column prior to starting the distillation operation was omitted. At the time of starting the distillation operation, the temperature of the outer wall surface of the distillation column, the temperature of the inner wall surface of the distillation column and the temperature of the packing material filled therein were 25° C., respectively.

The rise of the bottom pressure was observed from the start of the distillation operation. After 6 hours, since the bottom pressure and temperature reached 73 kPa and 89° C., respectively, the operation of the distillation column was stopped, and the inside of the distillation column was observed. As a result, it was recognized that acrylic acid polymers and ethyl acrylate polymers were adhered to a portion of the inner wall surface located above the raw material feed section, as well as the packing material in the vicinity thereof.

<Regarding Aspect (III) of the Invention>

Example 4

A stainless steel (SUS316) distillation column as shown in FIG. 5 having an inner diameter of 1,100 mm and a length of 20,000 mm, which was filled with an irregular packing material (IMTP) produced by Norton Inc., to form a packing material layer having a height of 8 m therein, and provided with 9 perforated plates underneath the packing material, was used to conduct the distillation of acrylic acid. The distillation column was operated at a raw material feed rate of 1,300 kg/hr, a bottom pressure of 7.9 kPa and a bottom temperature of 75° C., and upon stopping the operation thereof, the following procedure was conducted.

First, the supply of steam as a heating medium to the reboiler 58 of the distillation column 51 was interrupted, and the connection of the distillation column 51 to the raw material feed line was changed-over to an off-tank line to terminate the supply of the raw material thereto.

Next, the reboiler 58 was supplied with 30° C. re-cooled water instead of steam, and the bottom liquid of the distillation column 51 was circulated using the reboiler circulation pump 65 to rapidly cool the reboiler 58 and the bottom of the distillation column 51. Immediately after starting the rapid cooling procedure, a whole amount of 500 kg of acrylic acid at 40° C. in the reflux tank 56 was refluxed to the distillation column 51 from the top thereof to cool the inside of the distillation column 51.

After the elapse of 180 minutes from starting the stopping operation (stopping the supply of steam to the reboiler 58), the bottom temperature of the distillation column 51 reached 50° C., whereupon the supply of the inhibitor air to the bottom liquid of the distillation column 51 was interrupted. Further, the valve connecting an outlet of the reflux tank 56 with an ejector (not shown) was closed, and nitrogen gas was fed through the line 72 to return the inside pressure of the distillation column 51 to an ordinary pressure.

Meanwhile, upon the rapid cooling procedure, the inside pressure of the distillation column was 2.8 kPa, and the bottom temperature thereof was 70° C.

After stopping the distillation operation, the packing material was removed from the distillation column 51 to inspect the trays within the distillation column as well as the removed packing material. As a result, it was confirmed that no polymers were adhered to the trays and packing material.

Comparative Example 4

The same procedure as defined in Example 4 was conducted except that after interrupting the supply of steam to the reboiler 58, the reflux was stopped to remove the liquid in the reflux tank through the line 62b, and nitrogen was fed to the distillation column under such a condition that the bottom temperature of the distillation column 51 was kept at 70° C. without supplying the re-cooled water to the reboiler 58 in order to return the inside pressure of the distillation column to an ordinary pressure, thereby stopping the operation of the distillation column.

After stopping the distillation operation, the packing material was removed from the distillation column 51 to inspect the trays within the distillation column as well as the removed packing material. As a result, it was recognized that polymers were adhered to the trays and packing material, and it was therefore required to clean the trays and packing material.

<Regarding Aspects (IV) and (V) of the Invention>

Example 5

A stainless steel (SUS316) distillation column as shown in FIG. 5 having an inner diameter of 1,100 mm and a length of 20,000 mm, which was provided therein with 21 perforated plates (dual trays), was used to conduct the distillation of acrylic acid.

A mixture containing 98.5% by weight of acrylic acid, 0.3% by weight of maleic acid and 0.3% by weight of an acrylic acid dimer as crude (meth)acrylic acids was fed to the distillation column through the line 60 at 90° C. and a feed rate of 1,300 kg/hr. In addition, a solution prepared by dissolving 8% by weight of methoquinone in acrylic acid and a solution prepared by dissolving 1% by weight of phenothiazine in acrylic acid, were fed from the polymerization inhibitor-containing liquid tank 59 to the distillation column at feed rates of 34 kg/hr and 31 kg/hr, respectively. The distillation column was operated under a top pressure of 2.8 kPa and a bottom pressure of 7.9 kPa at a top temperature of 53° C. and a bottom temperature of 75° C., so that a high-purity acrylic acid having a purity of not less than 99.8% by weight was recovered from the top of the distillation column.

After 8 months, since the difference between the top and bottom pressures was increased, the operation of the distillation column was stopped to observe the inside thereof using an endoscope. As a result, it was recognized that polymers were present on the trays and, therefore, the inside of the distillation column was washed. Pure water was fed into the distillation column from the top thereof through the reflux tank 56 at a feed rate of 3 m³/hr for one hour. The water flowed down to the bottom of the distillation column was discharged out of the system through the bottom liquid removal line 63. Then, 8 wt. % aqueous ammonia at 25° C. was fed to the distillation column from the top thereof through the reflux tank 56 at a feed rate of 3 m³/hr for 40 minutes.

Next, the aqueous ammonia flowed down to the bottom of distillation column was circulated and fed to the top thereof through the reflux line using a pump equipped with a strainer at its suction side. After 3 hours, the circulation was stopped, and the bottom liquid was discharged through the bottom liquid removal line 63 out of the system. As a result of observing the inside of the distillation column using an endoscope, it was recognized that a slight amount of polymers were still present on the trays.

Next, 40° C. toluene was fed to the distillation column from the top thereof through the reflux tank 56 at a feed rate of 3 m³/hr for 40 minutes, and a similar procedure to the above circulation operation of the aqueous ammonia was performed for 3 hours. As a result of observing the inside of the distillation column using an endoscope, it was confirmed that no polymers were present on the trays. Then, the initially aimed operation of the distillation column for purifying the crude (meth)acrylic acids was restarted.

Example 6

The same procedure as defined in Example 1 was conducted except that the 8 wt. % aqueous ammonia and toluene were replaced with a 25 wt. % aqueous sodium hydroxide solution and methyl isobutyl ketone, respectively. The conditions of the inside of the distillation column in the respective steps were observed using an endoscope by the same method as defined in Example 1. As a result, the effectiveness of the present invention was confirmed.

Example 7

A stainless steel (SUS304) distillation column as shown in FIG. 5 having an inner diameter of 1,100 mm and a length of 26,000 mm which was provided therein with 36 perforated plates (dual trays), was used to conduct the distillation of ethyl acrylate.

A mixture containing 97.4% by weight of ethyl acrylate, 1.8% by weight of water, 0.4% by weight of acrylic acid, 0.4% by weight of ethanol and 0.1% by weight of ethyl acetate as crude (meth)acrylic acids was fed to the distillation column through the line 60 at a feed rate of 6,000 kg/hr. In addition, a solution prepared by dissolving 5% by weight of hydroquinone in ethanol was fed from the polymerization inhibitor-containing liquid tank 59 to the distillation column at a feed rate of 60 kg/hr. The distillation column was operated under a top pressure of 62.7 kPa and a bottom pressure of 72.7 kPa at a top temperature of 76° C. and a bottom temperature of 89° C., so that crude ethyl acrylate having a purity of not less than 99.1% by weight was recovered from the bottom of the distillation column.

After 10 months, since the difference between the top and bottom pressures was increased, the operation of the distillation column was stopped to observe the inside thereof using an endoscope. As a result, it was confirmed that polymers were present on the trays and, therefore, the inside of the distillation column was washed. Pure water was fed into the distillation column from the top thereof through the reflux tank 56 at a feed rate of 4 m³/hr for one hour. The water flowed down to the bottom of the distillation column was discharged out of the system through the bottom liquid removal line 63. Then, 7 wt. % aqueous ammonia at 25° C. was fed to the distillation column from the top thereof through the reflux tank 56 at a feed rate of 4 m³/hr for 30 minutes.

Next, the aqueous ammonia flowed down to the bottom of distillation column was circulated and fed to the top thereof through the reflux line using a pump equipped with a strainer at its suction side. After 3 hours, the circulation was stopped, and the bottom liquid was discharged out of the system through the bottom liquid removal line 63. As a result of observing the inside of the distillation column using an endoscope, it was recognized that a slight-amount of polymers were still present on the trays.

Next, 40° C. ethanol was fed to the distillation column from the top thereof through the reflux tank 56 at a feed rate of 4 m³/hr for 40 minutes, and a similar procedure to the above circulation operation of the aqueous ammonia was performed for 3 hours. As a result of observing the inside of the distillation column using an endoscope, it was confirmed that no polymers were present on the trays. Then, the initially aimed operation of the distillation column for purifying the crude (meth)acrylic acids was restarted.

Example 8

The same procedure as defined in Example 7 was conducted except that the 7 wt. % aqueous ammonia was replaced with a 25 wt. % aqueous sodium hydroxide solution. As a result of observing the conditions of the inside of the distillation column in the respective steps using an endoscope by the same method as defined in Example 7, the effectiveness of the present invention was confirmed.

Comparative Example 5

The same procedure as defined in Example 5 was conducted except that toluene was replaced with water. As a result of observing the conditions of the inside of the distillation column in the respective steps using an endoscope by the same method as defined in Example 5, it was recognized that a slight amount of polymers were still present on the trays.

Comparative Example 6

The same procedure as defined in Example 6 was conducted except that methyl isobutyl ketone was replaced with water. As a result of observing the conditions of the inside of the distillation column in the respective steps using an endoscope by the same method as defined in Example 6, it was recognized that a slight amount of polymers were still present on the trays.

Comparative Example 7

The same procedure as defined in Example 7 was conducted except that ethanol was replaced with water. As a result of observing the conditions of the inside of the distillation column in the respective steps using an endoscope by the same method as defined in Example 7, it was recognized that a slight amount of polymers were still present on the trays.

Comparative Example 8

The same procedure as defined in Example 8 was conducted except that ethanol was replaced with water. As a result of observing the conditions of the inside of the distillation column in the respective steps using an endoscope by the same method as defined in Example 8, it was recognized that a slight amount of polymers were still present on the trays.

Example 9

After the second water-washing step conducted for 3 hours and 40 minutes in Comparative Example 5, 40° C. toluene was further fed to the distillation column from the top thereof through the reflux tank 56 at a feed rate of 3 m³/hr for 40 minutes, and a similar procedure to the circulation operation of the aqueous ammonia was performed for 3 hours. As a result of observing the conditions of the inside of the distillation column using an endoscope, it was confirmed that no polymers were present on the trays. Then, the initially aimed operation of the distillation column for purifying the crude (meth)acrylic acids was restarted.

Example 10

After the second water-washing step conducted for 3 hours and 40 minutes in Comparative Example 6, 40° C. methyl isobutyl ketone was further fed to the distillation column from the top thereof through the reflux tank 56 at a feed rate of 3 m³/hr for 40 minutes, and a similar procedure to the circulation operation of the aqueous ammonia was performed for 3 hours. As a result of observing the conditions of the inside of the distillation column using an endoscope, it was confirmed that no polymers were present on the trays. Then, the initially aimed operation of the distillation column for purifying the crude (meth)acrylic acids was restarted.

Example 11

The same procedure as defined in Example 9 was conducted except that toluene used for the organic solvent-washing step was replaced with crude (meth)acrylic acids as the raw liquid to be distilled. As a result of observing the conditions of the inside of the distillation column in the respective steps using an endoscope by the same method as defined in Example 9, the effectiveness of the present invention was confirmed.

<Regarding Aspect (VI) of the Invention>

Example 12

A stainless steel (SUS316) distillation column as shown in FIG. 5 having an inner diameter of 1,100 mm and a length of 20,000 mm which was filled with an irregular packing material (IMTP) produced by Norton Inc., to form a packing material layer having a height of 8 m therein, and provided with 9 perforated plates underneath the packing material layer, was used to conduct the distillation of acrylic acid. Prior to the distillation, the inner wall surface of the distillation column was subjected to the following wetting procedure.

First, 20 kg of a solution prepared by dissolving 8% by weight of methoquinone as a polymerization inhibitor in acrylic acid was fed together with 500 kg of acrylic acid supplied into the reflux tank 56, to the distillation column from the top thereof. In addition, 40 kg of a solution prepared by dissolving 1% by weight of phenothiazine as a polymerization inhibitor in acrylic acid was fed to the distillation column through the raw material feed line 60. The thus introduced liquid was flowed down to the bottom of the distillation column while wetting the inner wall surface thereof. The liquid collected on the bottom of the distillation column was fed again through the raw material feed line 60 at a feed rate of 1,300 kg/hr, and the circulation procedure was continued for about one hour. About 30 minutes after completion of the circulation procedure, a mixture containing 98.5% by weight of acrylic acid, 0.3% by weight of maleic acid and 0.3% by weight of an acrylic acid dimer as an acrylic monomer was fed to the distillation column at a feed rate of 1,300 kg/hr. Further, a solution prepared by dissolving 8% by weight of methoquinone in acrylic acid and a solution prepared by dissolving 1% by weight of phenothiazine in acrylic acid were fed from the polymerization inhibitor-containing liquid tank 59 at feed rates of 34 kg/hr and 31 kg/hr, respectively. The distillation column was further supplied with a heat source, and then controlled in inside pressure, etc. After about 5 hours, the operation of the distillation column was stabilized under a top pressure of 2.8 kPa and a bottom pressure of 7.9 kPa at a top temperature of 53° C. and a bottom temperature of 75° C. As a result, high-purity acrylic acid having a purity of not less than 99.8% by weight was recovered from the top of the distillation column. During the distillation operation, the difference between the to and bottom pressures (hereinafter referred to as "pressure difference") was stabilized, and it was possible to continuously perform the distillation operation for one year.

Comparative Example 9

The same procedure as defined in Example 12 was conducted except that the wetting procedure for the inner wall surface of the distillation column was omitted. The pressure difference within the distillation column was raised from initiation of the distillation operation, and reached 12 kPa after the elapse of 87 days. At that time, since the acrylic acid recovered from the top of the distillation column was deteriorated in purity, and the liquid was no longer dropped to the bottom thereof, the distillation operation was stopped. As a result of observing the conditions of the inside of the distillation column after stopping its operation, it was recognized that a large amount of polymers were adhered to the packing material as well as the trays.

Example 13

The same procedure as defined in Example 12 was conducted except that the perforated plates were replaced with the irregular packing material (IMTP) produced by Norton Inc., to form a packing material layer having a height of 6 m. The distillation column was further supplied with a heat source, and then controlled in inside pressure, etc. After about 4 hours, the operation of the distillation column was stabilized under a top pressure of 2.8 kPa and a bottom pressure of 7.5 kPa at a top temperature of 53° C. and a bottom temperature of 72° C. As a result, high-purity acrylic acid having a purity of not less than 99.8% by weight was recovered from the top of the distillation column. During the distillation operation, the pressure difference was stabilized, and it was possible to continuously perform the distillation operation for one year.

Comparative Example 10

The same procedure as defined in Example 13 was conducted except that the wetting procedure for the inner wall surface of the distillation column was omitted. The pressure difference within the distillation column was raised from initiation of the distillation operation, and reached 15 kPa after the elapse of 62 days. At that time, since the acrylic acid recovered from the top of the distillation column was deteriorated in purity, and the liquid was no longer dropped to the bottom thereof, the distillation operation was stopped. As a result of observing the conditions of the inside of the distillation column after stopping its operation, it was recognized that a large amount of polymers were adhered to the packing material.

Example 14

The same procedure as defined in Example 12 was conducted except that the irregular packing material (IMTP) produced by Norton Inc., was replaced with 12 perforated plates. The distillation column was further supplied with a heat source, and then controlled in inside pressure, etc. After about 6 hours, the operation of the distillation column was stabilized under a top pressure of 2.8 kPa and a bottom pressure of 8.4 kPa at a top temperature of 53° C. and a bottom temperature of 78° C. As a result, high-purity acrylic acid having a purity of not less than 99.8% by weight was recovered from the top of the distillation column. During the distillation operation, the pressure difference was stabilized, and it was possible to continuously perform the distillation operation for one year.

Comparative Example 11

The same procedure as defined in Example 14 was conducted except that the wetting procedure for the inner wall surface of the distillation column was omitted. The pressure difference within the distillation column was raised from initiation of the distillation operation, and reached 11 kPa after the elapse of 123 days. At that time, since the acrylic acid recovered from the top of the distillation column was deteriorated in purity, and the liquid was hardly dropped to the bottom thereof, the distillation operation was stopped. As a result of observing the conditions of the inside of the distillation column after stopping its operation, it was recognized that a large amount of polymers were adhered to the perforated plates.

Example 15

A stainless steel (SUS304) distillation column as shown in FIG. 5 having an inner diameter of 1,100 mm and a length of 26,000 mm which was filled with an irregular packing material (IMTP) produced by Norton Inc., to form a packing material layer having a height of 13 m therein, was used to conduct the distillation of crude ethyl acrylate. Prior to the distillation, the inner wall surface of the distillation column was subjected to the following wetting procedure.

First, 21 kg of a solution prepared by dissolving 5% by weight of hydroquinone as a polymerization inhibitor in ethanol was fed together with 600 kg of ethanol supplied into the reflux tank 56, to the distillation column from the top thereof. The thus introduced liquid was flowed down to the bottom of the distillation column while wetting the inner wall surface thereof. The liquid collected on the bottom of the distillation column was fed again through the raw material feed line 60 at a feed rate of 6,000 kg/hr, and the circulation procedure was continued for about one hour. About 30 minutes after completion of the circulation procedure, a mixture containing 97.4% by weight of ethyl acrylate, 1.8% by weight of water, 0.4% by weight of acrylic acid, 0.4% by weight of ethanol and 0.1% by weight of ethyl acetate as an acrylic monomer was fed to the distillation column at a feed rate of 6,000 kg/hr. Further, a solution prepared by dissolving 5% by weight of hydroquinone in ethanol was fed to the distillation column from the polymerization inhibitor-containing liquid tank 59 at a feed rate of 60 kg/hr. The distillation column was further supplied with a heat source, and then controlled in inside pressure, etc. After about 6 hours, the operation of the distillation column was stabilized under a top pressure of 62.7 kPa and a bottom pressure of 69.3 kPa at a top temperature of 76° C. and a bottom temperature of 84° C. As a result, high-purity crude ethyl acrylate having a purity of not less than 99.1% by weight was recovered from the bottom of the distillation column. During the distillation operation, the pressure difference within the distillation column was stabilized, and it was possible to continuously perform the distillation operation for one year.

Comparative Example 12

The same procedure as defined in Example 15 was conducted except that the wetting procedure for the inner wall surface of the distillation column was omitted. The pressure difference within the distillation column was raised from initiation of the distillation operation, and reached 31 kPa after the elapse of 98 days. At that time, since the ethyl acrylate recovered from the bottom of the distillation column was deteriorated in purity, and the liquid was no longer dropped to the bottom thereof, the distillation operation was stopped. As a result of observing the conditions of the inside of the distillation column after stopping its operation, it was recognized that a large amount of polymers were adhered to the packing material.

Example 16

The same procedure as defined in Example 15 was conducted except that the irregular packing material (IMTP) produced by Norton Inc., was replaced with 36 perforated plates (dual trays). The distillation column was further supplied with a heat source, and then controlled in inside pressure, etc. After about 7 hours, the operation of the distillation column was stabilized under a top pressure of 62.7 kPa and a bottom pressure of 72.7 kPa at a top temperature of 76° C. and a bottom temperature of 89° C. As a result, high-purity ethyl acrylate having a purity of not less than 99.1% by weight was recovered from the bottom of the distillation column. During the distillation operation, the pressure difference was stabilized, and it was possible to continuously perform the distillation operation for one year.

Comparative Example 13

The same procedure as defined in Example 16 was conducted except that the wetting procedure for the inner wall surface of the distillation column was omitted. The pressure difference within the distillation column was raised from initiation of the distillation operation, and reached 37 kPa after the elapse of 153 days. At that time, since the ethyl acrylate recovered from the bottom of the distillation column was deteriorated in purity, and the liquid was hardly dropped to the bottom thereof, the distillation operation was stopped. As a result of observing the conditions of the inside of the distillation column after stopping its operation, it was recognized that a large amount of polymers were adhered to the perforated plates.

Example 17

A stainless steel (SUS304) distillation column as shown in FIG. 5 having an inner diameter of 1,100 mm and a length of 18,000 mm which was provided therein with 25 sieve trays, was used to conduct the distillation of ethyl acrylate-containing water as an acrylic monomer. Prior to the distillation, the inner wall surface of the distillation column was subjected to the following wetting procedure.

First, 52 kg of a solution prepared by dissolving 5% by weight of hydroquinone as a polymerization inhibitor in ethanol was fed together with 1,300 kg of ethanol supplied into the reflux tank 56, to the distillation column from the top thereof. The thus introduced liquid was flowed down to the bottom of the distillation column while wetting the inner wall surface thereof. The liquid collected on the bottom of the distillation column was fed again to the top of the distillation column through the raw material feed line 60 at a feed rate of 18,300 kg/hr, and the circulation procedure was continued for about one hour. About 30 minutes after completion of the circulation procedure, a mixture containing 2.2% by weight of ethyl acrylate, 90.7% by weight of water, 0.1% by weight of acrylic acid and 7.0% by weight of ethanol as an acrylic monomer was fed to the distillation column at a feed rate of 18,300 kg/hr. Further, a solution prepared by dissolving 5% by weight of hydroquinone in ethanol was fed to the distillation column from the polymerization inhibitor-containing liquid tank 59 at a feed rate of 18 kg/hr. The distillation column was further supplied with a heat source, and then controlled in inside pressure, etc. After about 4 hours, the operation of the distillation column was stabilized under a top pressure of 62.7 kPa and a bottom pressure of 76.0 kPa at a top temperature of 66° C. and a bottom temperature of 92° C. As a result, an ethyl acrylate solution containing 67% by weight of ethanol, 21% by weight of ethyl acrylate and 12% by weight of water was recovered from the top of the distillation column. During the distillation operation, the pressure difference within the distillation column was stabilized, and it was possible to continuously perform the distillation operation for one year.

Comparative Example 14

The same procedure as defined in Example 17 was conducted except that the wetting procedure for the inner wall surface of the distillation column was omitted. The pressure difference within the distillation column was gradually raised from initiation of the distillation operation, and reached 40 kPa after the elapse of 238 days. At that time, since the ethyl acrylate recovered from the top of the distillation column was deteriorated in purity, and the liquid was no longer dropped to the bottom thereof, the distillation operation was stopped. As a result of observing the conditions of the inside of the distillation column after stopping its operation, it was recognized that a large amount of polymers were adhered to the trays.

<Regarding Aspect (VII) of the Invention>

(Preparation of Test Piece)

A flask was filled with 90% by weight of acrylic acid, 7% by weight of toluene, 2% by weight of acetic acid, 0.8% by weight of water and 40 ppm by weight of p-methoxyphenol. Further, a 2 cm-square plate made of stainless steel (SUS316) was placed so as immerse in the liquid filled in the flask. The contents of the flask were heated at 92° C. under an ordinary pressure for 8 hours. Then, a condenser was fitted to an upper portion of the flask so as to cause substantially no liquid in the flask to be vaporized. After allowing the thus arranged apparatus to stand for cooling, it was confirmed that the inner wall surface of the flask and the metal plate immersed therein were covered with white-colored polymers. The metal plate was transferred into a separate container filled with acrylic acid, and preserved therein until use thereof.

(Washing Test 1)

The above prepared test piece was washed using a glass distillation testing apparatus. A distillation column portion of the testing apparatus was constituted of a glass cylinder having an inner diameter of 50 mm and a height of 900 mm. A 1-liter flask was placed on a bottom of the column, and an oil bath as an overheating source was placed underneath the flask. In addition, a condenser was fitted to a top of the column so as to allow a whole amount in the column to be refluxed at 25° C. Further, a reflux line extending from the condenser was opened at one point thereof to atmospheric air such that an inside of the distillation apparatus was always kept under atmospheric pressure.

A lowest portion of the glass cylinder was filled with steel wool to form a steel wool layer of 10 mm in height, on which were successively filled the test piece, steel wool of 20 mm in height, Rashig ring of 300 mm in height, steel wool of 20 mm in height, additional test piece and steel wool of 10 mm in height.

Then, 5 wt. % aqueous ammonia was filled in the cylinder, and refluxed at a bottom temperature of 99° C. for one hour. After allowing the cylinder to stand for cooling to room temperature, the test pieces were removed from the cylinder. As a result, it was confirmed that substances adhered to surfaces of both the test pieces placed on upper and lower portions of the cylinder all were washed away.

(Washing Test 2)

The same procedure as defined in Washing Test 1 was conducted except that a 5 wt. % aqueous sodium hydroxide solution was filled in the cylinder and refluxed (the bottom temperature was 103° C.). After allowing the cylinder to stand for cooling to room temperature, the test pieces were removed from the cylinder. As a result, it was confirmed that substances adhered to the surface of the test piece placed on a lower portion of the cylinder were washed away, but substances adhered to the surface of the test piece placed on a lower portion of the cylinder still remained.

Reference Example

During the step of obtaining the crude acrylic acid by concentrating the raw material in the presence of an azeotropic agent (toluene) (in the dehydration distillation column), a part of deposits in the dehydration distillation column were sampled upon stopping its operation before washing an inside of the column, and subjected to the following dissolution tests using a base solution.

(1) The thus sampled deposits were immersed for 3 hours in a 5 wt. % aqueous ammonia heated to 50° C. The deposits were swelled up four or more times an initial volume thereof when visually observed, and an extremely thin sheet-like solid was separated therefrom. The resultant solution was a colored transparent liquid, and readily naturally filtered through a 1 mµ-mesh filter paper.

(2) The thus sampled deposits were immersed for 3 hours in a 5 wt. % aqueous sodium hydroxide solution heated to 50° C. The deposits were swelled up four or more times an initial volume thereof when visually observed, so that gelled substances were obtained. Although it was attempted to filter the resultant gel under a pressure up to 2 atm through a 3 mµ-mesh filter paper, clogging of the filter paper was immediately caused, and the filtration was substantially impossible.

INDUSTRIAL APPLICABILITY

As described above, according to the present invention, in the stopping and starting operations of a distillation column for production of (meth)acrylic acids, it is possible to early and safely stop the operation of the distillation column while preventing the occurrence of polymerization within the distillation column, thereby stably performing an operation for distillation of acrylic monomers for a long period of time. Also, according to the present invention, it is possible to effectively wash out and remove solids adhered onto a rear side of the respective trays fitted in the distillation column. Accordingly, the present invention can provide high industrial values.

What is claimed is:

1. A process for producing purified (meth)acrylic acid by distilling acrylic acid, or methacrylic acid or an ester of acrylic acid or methacrylic acid using a distillation column, the process comprising:
    (a) stopping the distillation column,
    (b) successively washing the distillation column with the following washing agents:
    (1) water;
    (2) an aqueous alkali solution; and
    (3) an organic solvent and
    (c) re-starting the distillation column.

2. A process for producing purified (meth)acrylic acid by distilling acrylic acid, methacrylic acid or an ester of acrylic acid or methacrylic acid using a distillation column, the process comprising:
    (a) stopping the distillation column,
    (b) successively washing the distillation column with the following washing agents:
    (1) water;
    (2) an aqueous alkali solution;
    (2a) water; and
    (3) an organic solvent, and
    (c) re-starting the distillation column.

3. A process according to claim 1, wherein an azeotropic agent used upon condensation of an aqueous solution containing (meth)acrylic acid is used as the organic solvent.

4. A process according to claim 1, wherein crude (meth)acrylic acid obtained before stopping the operation of the distillation column are used as the organic solvent.

5. A process according to claim 1, wherein the purified (meth)acrylic acid obtained before stopping the operation of the distillation column are used as the organic solvent.

6. A process according to claim 1, wherein a bottom liquid of the distillation column, which is obtained before stopping the operation of the distillation column is used as the organic solvent.

7. process according to claim 1, wherein said organic solvent contains water in an amount of not more than 2% by weight.

8. A process according to claim 1, wherein said aqueous alkali solution is an aqueous alkali hydroxide solution having a concentration of 1 to 25% by weight.

9. A process according to claim 1, wherein said aqueous alkali solution is aqueous ammonia having a concentration of 1 to 25% by weight.

* * * * *